(12) United States Patent
Bates et al.

(10) Patent No.: US 8,394,930 B2
(45) Date of Patent: Mar. 12, 2013

(54) GROWTH FACTOR ISOFORM

(75) Inventors: David O. Bates, Bishopston Bristol (GB); Steven J. Harper, Tintern Gwent (GB)

(73) Assignee: University of Bristol, Bristol (GB)

( * ) Notice: Subject to any disclaimer, the term of this patent is extended or adjusted under 35 U.S.C. 154(b) by 0 days.

(21) Appl. No.: 12/768,365

(22) Filed: Apr. 27, 2010

(65) Prior Publication Data

US 2010/0305034 A1   Dec. 2, 2010

Related U.S. Application Data

(62) Division of application No. 10/485,539, filed as application No. PCT/GB02/03213 on Jul. 12, 2002, now Pat. No. 7,820,178.

(30) Foreign Application Priority Data

Aug. 1, 2001   (GB) .................................... 0118836.6
Feb. 6, 2002   (GB) .................................... 0202817.3

(51) Int. Cl.
    *C07K 16/00*   (2006.01)
(52) U.S. Cl. ................ 530/387.9; 530/387.1; 530/389.1; 530/389.2
(58) Field of Classification Search .................. None
    See application file for complete search history.

(56) References Cited

PUBLICATIONS

Brockelsby et al., Lab Invest 1999; 79:1101-1111.*

* cited by examiner

*Primary Examiner* — Daniel C Gamett
(74) *Attorney, Agent, or Firm* — Nixon Peabody LLP; Ronald I. Eisenstein; Leena H. Karttunen Contarino

(57) ABSTRACT

An isolated VEGF polypeptide having anti-angiogenic activity, said polypeptide including the amino acid sequence of SEQ.ID NO.1, or variants thereof.

1 Claim, 24 Drawing Sheets

```
                                    Exon 7/8 boundary
nt 518                                                                                              608
VEGF 165   AAGGCGAGGCAGCTTGAGTTAAACGAACGTACTTGCAGATGTGACAAGCCGAGGCGGTGAGCCGGGCAGGAGGAAGGAGCCTCCCTCAGGGT
VEGF 165b  AAGGCGAGGCAGCTTGAGTTAAACGAACGTACTTGCAG nt         609                                                    666
VEGF 165   TTCGGGAACCAGATCTCTCACCAGGAAAGACTGATACAGAACGATCGATACAGAAAACCAC  [SEQ ID NO: 19]
VEGF 165b         ATCTCTCACCAGGAAAGACTGATACAGAACGATCGATACAGAAAACCAC  [SEQ ID NO: 27]
```

FIG. 4A

```
                     146                Exon 7                                       158
aa     Thr Asp Ser Arg Cys Lys Ala Arg Gln Leu Glu Leu Asn Glu Arg Thr Cys Ar       intron
       ACA GAC TCG CGT TGC AAG GCG AGG CAG CTT GAG TTA AAC GAA CGT ACT TGC AG gttggttcccagaggca Amino acid no                           160        Exon 8                165
               intron         g Cys Asp Lys Pro Arg Arg    *
       ...ttttccatttccctcag A TGT GAC AAG CCG AGG CGG TGA gccgggcaggagggaaggagcctcc Exon 9                         165
aa no                      g Ser Leu Thr Arg Lys Asp  *        3'UTR
       ctcagggtttcgggaaccag A TCT CTC ACC AGG AAA GAC TGA tacagaacgatcgatacagaaaccac
       3'UTR (Ex 8)/intron (Ex9)
```

*FIG. 4B*

VEGF₁₆₅  Thr Asp Ser Arg Cys Lys Ala Arg Gln Leu Glu Leu Asn Glu Arg Thr Cys Arg Cys Asp Lys Pro Arg Arg * [SEQ ID NO: 20]

VEGF₁₆₅  Thr Asp Ser Arg Cys Lys Ala Arg Gln Leu Glu Leu Asn Glu Arg Thr Cys Arg Ser Leu Thr Arg Lys Asp * [SEQ ID NO: 31]

*FIG. 4C*

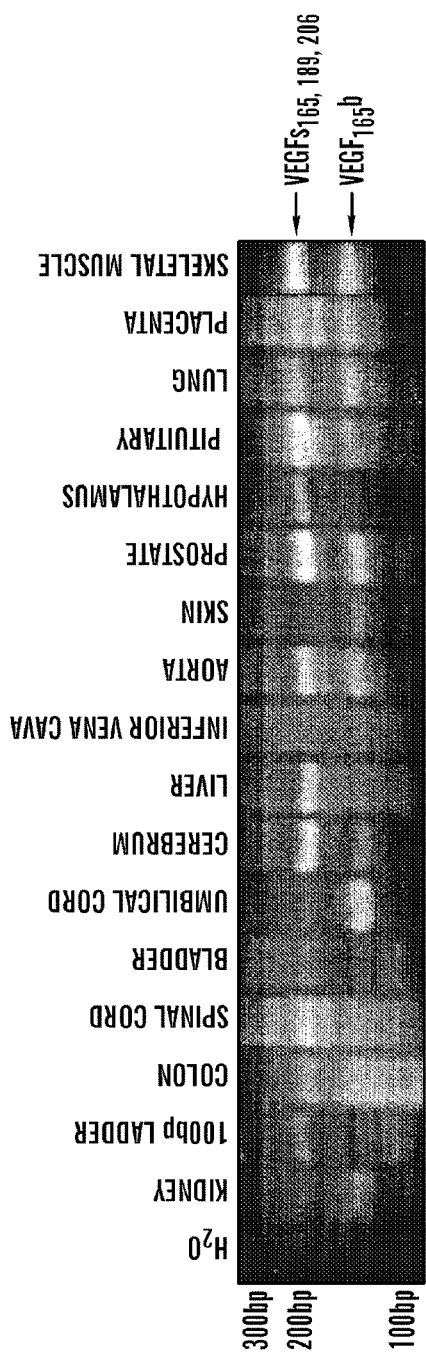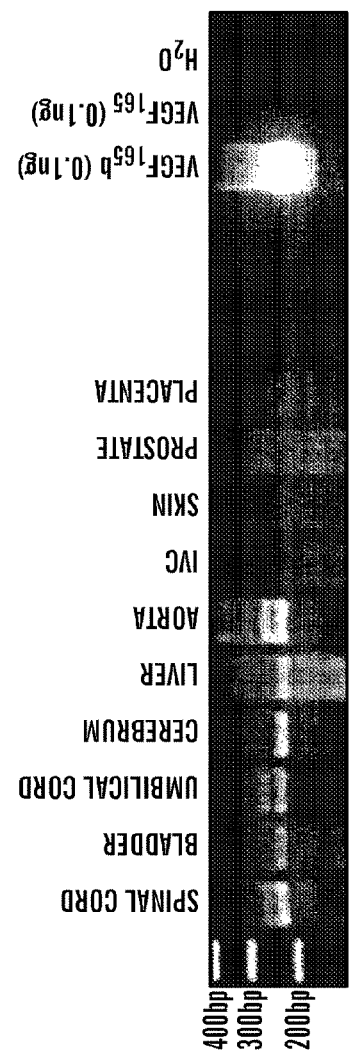
FIG. 10A
FIG. 10B

ACGTCTCACCAGGAAAGACTGA CACAGAACTACCATAGCCCCGGCCACCACCACCACCACCACCAC - BOVINE [SEQ ID NO:21]
ATCTCTCACCAGGAAAGACTGA TACAGAACGATCGATACAGAAACCACGCTGCCACCACACCATC?A - HUMAN [SEQ ID NO:22]
ACCTCTCACC-GGAAAGACCGA TTAACATGTCACCATGCCATCATCGTCACGTTGACAGAACAG - MURINE 3' [SEQ ID NO:23]

|—EXON 9—|—3'UTR—|

FIG. 12A

GROWTH FACTOR ISOFORM

REFERENCE TO RELATED APPLICATIONS

This application is a divisional application of U.S. application Ser. No. 10/485,539 filed on Aug. 31, 2004, now U.S. Pat. No. 7,820,178 issued on Oct. 26, 2010, which is a 371 National Phase Application of International Application No. PCT/GB02/03213, filed Jul. 12, 2002, which claims priority to GB Application No. 0118836.6 filed Aug. 1, 2001, and GB Application No. 0202817.3 filed Feb. 6, 2002 the entire disclosures of each of which are incorporated herein by reference.

SEQUENCE LISTING

In accordance with 37 CFR 1.52(e)(5), a Sequence Listing in the form of a text file (entitled "SequenceListing.txt," created on Apr. 12, 2010, and 10 kilobytes in size) is incorporated herein by reference in its entirety.

The present invention relates to novel VEGF isoforms and their use as anti-angiogenic, anti-vasodilatory, anti-permeability and anti-proliferative agents and inhibition of such isoforms in conditions in which their expression in excess may be associated with disease states.

In order for tissue to grow it needs to develop and maintain an active and highly efficient blood supply from the surrounding vasculature. This process (angiogenesis) is necessary for progression and survival of tumours, development of rheumatoid arthritis, psoriasis, proliferative eye disease and a host of other pathologies. A number of new anti-tumour therapies are being developed that target this novel vasculature, or the growth factors that produce it. This is of particular interest in cancer research. This novel approach to cancer therapy contrasts with traditional chemotherapeutic strategies which target cell proliferation. The advantage of this approach lies in the distinction that angiogenesis is not an essential component of normal physiology (except in the development of the corpus luteum, endometrium and placenta in pre-menopausal women), and therefore anti-angiogenesis is not as toxic as anti-proliferative therapies, which also affect hair growth, normal gastrointestinal physiology, skin epidermis and many other normal aspects of physiology. The therapeutic dose of anti-angiogenics is therefore predicted to be well below the most tolerated doses, unlike anti-proliferative drugs. Tumours develop and maintain their new blood supply by secreting endothelial cell-specific growth factors, a number of which have been isolated in the last few years. One of these is Vascular Endothelial Growth Factor (VEGF), a naturally secreted protein that stimulates angiogenesis, vasodilatation and increased vascular permeability in vivo.

Vascular endothelial growth factor (VEGF) is a 32-42 kDa dimeric glycoprotein which mediates vasodilatation, increased vascular permeability and endothelial cell mitogenesis. Differential exon splicing of the VEGF gene results in three main mRNA species which code for three secreted isoforms (subscripts denote numbers of amino acids): $VEGF_{189}$, $VEGF_{165}$, and $VEGF_{121}$. A number of minor splice variants have been described ($VEGF_{206}$, $VEGF_{183}$, $VEGF_{145}$ and $VEGF_{148}$) but their importance remains uncertain (FIG. 1). Each isoform has distinct properties and patterns of expression (Ferrara et al (1997) Endocr. Rev. 18, 4-25; Houck et al (1991) Mol. Endocrinol. 5, 1806-1814; Poltorak et al (1997) J. Biol. Chem. 272, 7151-7158; Simon et al (1995) Am. J. Physiol. 268, 240-250; Brown et al (1992) Kidney Int. 42, 1457-1461; Park et al (1993) Mol. Biol. Cell 4, 1317-1326; Kevt et al (1996) J. Biol. Chem. 271, 7788-7795; Jingling et al (1999) Invest Opthalmol Vis Sci 40(3):752-9; Plouet et al (1997) J. Biol. Chem 272, 13390-13396; and Whittle C et al Clin Sci (1999) 97, 303-312). The various molecular forms of VEGF share a common amino-terminal domain consisting of 110 amino acids, but differ in the length of the carboxyl-terminal portion and the final 6 amino acid residues (coded for by exon 8) are identical in all isoforms previously described except $VEGF_{148}$.

VEGF is known to promote vascular endothelial cell proliferation and angiogenesis, which are important components of a variety of pathologies, including tumour growth and metastasis, rheumatoid arthritis, atherosclerosis and arteriosclerosis (Celleti et al Nature 2001; 7. 425-9; Lemström et al 2002, 105. 2524-2530), neointimal hyperplasia, diabetic retinopathy and other complications of diabetes, trachoma, retrolental fibroplasia, neovascular glaucoma, age-related macular degeneration, trachoma haemangiomata, immune rejection of transplanted corneal tissue, corneal angiogenesis associated with ocular injury or infection, psoriasis, gingivitis and other conditions known to be associated with angiogenesis and/or chronic inflammation. Corneal angiogenesis associated with ocular injury or infection may be caused, for example, by Herpes or other viral or microbial infection.

In addition VEGF expression and angiogenesis are increased during fat deposition in animal models (Fredriksson et al (2000), J. Bio.Chem. 275(18): 13802-11; Asano et al (1999) J. Vet. Med. Sci. 61(4):403-9; Tonello et al (1999) FEBS Lett 442(2-3): 167-72; Asano et al (1997) Biochem. J. 328(Pt.1): 179-83), and it is therefore possible that anti-angiogenic agents may be used for reducing fat deposition and for fat reduction.

VEGF may also mediate pre-eclampsia (Brockelsby et al 1999, Lab Invest 79:1101-11). Pre-eclampsia is a condition of pregnancy characterised by high blood pressure, persistent excessive swelling of the hands, feet, ankles and sometimes face, and protein in the urine. If not diagnosed and treated quickly, it can lead to eclampsia, where a seizure occurs, coupled with a sharp rise in blood pressure and serious risk of stroke, as well as extreme distress to an unborn baby. Dysregulation of vasoconstriction/vaso-dilatation is known to be an important component of pre-eclampsia. Despite the fact that VEGF has been implicated in pre-eclampsia, one paradox is as yet unexplained; pre-eclampsia is associated with hypertension and vasoconstriction but $VEGF_{165}$ is a well known vasodilator.

VEGF also increases endothelial permeability which is an important component of a different variety of conditions including angiogenesis related oedema (i.e. in tumours), septicaemic/endotoxaemic shock, nephrotic syndrome, lymphoedema, burns and adult respiratory distress syndrome (ARDS) and pre-eclampsia as above.

The endothelial proliferative activity of VEGF is mediated by two high affinity membrane-bound tyrosine kinase receptors: VEGF receptor 1 ($VEGFR_1$, flt-1(fms-like tyrosine kinase-1)); and VEGF receptor 2 ($VEGFR_2$, flk (foetal liver kinase), KDR (Kinase domain containing receptor)). These receptors are expressed by vascular endothelial cells.

It is believed that normally both of the VEGF receptors are stimulated by a homodimer of VEGF monomers interacting with a homodimer of receptor molecules.

In view of the implied role of VEGF-mediated receptor stimulation in various diseases, there is considerable interest in developing inhibitors that would interfere with or modulate the interaction between VEGF and its receptor.

The major obstacle to the development of novel anti-angiogenic drugs in oncology and other specialities, however, has been the difficulty in obtaining angiogenic-specific inhibitors with acceptable half lives, solubility, specificity and immunotolerance.

Tissues are normally in an angiogenesis equilibrium, i.e. growth factors which stimulate new vessel growth are balanced by other factors which inhibit vessel growth (M. L. IruelaArispe and H. F. Dvorak, (1997) *Thrombosis and Haemostasis.* (78): 672-677). One of the tissues in which VEGF is normally most highly expressed is in the kidney glomerulus (L. F. Brown, et al., (1992) *Kidney Int.* (42):1457-61; E. Bailey 1999 J Clin Pathol 52, 735-738.). This tissue expresses high levels of VEGF, has very high endothelial permeability (an action of VEGF), but has low levels of angiogenesis. The reason for the high VEGF expression levels in kidney is not known but the high permeability of the endothelium and high glomerular filtration rate both appear to depend on VEGF (B. Klanke, et al., (1998) *Nephrol Dial Transplant*, (13):875-850) (C. Whittle, et al., (1999) *Clin Sci (Colch)*. (97):303-12). It is not understood why there is no angiogenesis in kidneys in the presence of such high expression of VEGF.

The present inventors have identified a new isoform of VEGF in kidney cells, which is differentially spliced into a previously undescribed exon, exon 9. This novel isoform has been designated $VEGF_{165}b$.

According to a first aspect of the invention, there is provided an isolated VEGF polypeptide having anti-angiogenic activity, said polypeptide including the amino acid sequence of SEQ.ID NO.1, or variants thereof.

This unexpected anti-angiogenic property of the polypeptide of the first aspect of the present invention contrasts completely with the properties of all previously described VEGF isoforms which are pro-angiogenic.

The term "isolated" as used herein means altered from its natural state, i.e., if it occurs in nature, it has been changed or removed from its original environment, or both. For example, a polynucleotide or a polypeptide naturally present in a living organism is not "isolated", but the same polynucleotide or polypeptide separated from the coexisting materials of its natural state is "isolated", as the term is used herein. Moreover, a polynucleotide or polypeptide that is introduced into an organism by transformation, genetic manipulation or by another recombinant method is "isolated" even if it is still present in said organism, which organism can be living or non-living.

The term "variant(s)" as used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and/or truncations in the polypeptide encoded by the reference sequence, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions, additions, and/or deletions in any combination. A substituted or inserted amino acid residue may or may not be one encoded by the genetic code. The present invention also includes variants of each of the polypeptides of the invention, that is polypeptides that vary from the references by conservative amino acid substitutions, whereby a residue is substituted by another with like characteristics. Typical conservative amino acid substitutions are among Ala, Val, Leu and Ile; among Ser and Thr; among the acidic residues, Asp and Glu; among Asn and Gln; and among the basic residues Lys and Arg; or aromatic residues Phe and Tyr. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

Such conservative variations can further include the following:

| Original Residue | Variation |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of variations selected can be based on the analysis of the frequencies of amino acid variations between homologous proteins of different species developed by Schulz et al. (*Principles of Protein Structure*, Springer-Verlag, 1978), on the analyses of structure-forming potentials developed by Chou and Fasman (*Biochemistry* 13:211, 1974 and *Adv. Enzymol.*, 47:45-149, 1978), and on the analysis of hydrophobicity patterns in proteins developed by Eisenberg et al. (*Proc. Natl. Acad. Sci. USA* 81:140-144, 1984), Kyte & Doolittle (*J. Molec. Biol.* 157: 105-132, 1981), and Goldman et al. (*Ann. Rev. Biophys. Chem.* 15:321-353, 1986). Particularly preferred are variants in which several, e.g., 5-10, 1-5, 1-3, 1-2 or 1 amino acids are substituted, deleted, or added in any combination. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to a person skilled in the art.

The term "nucleotide(s)" as used herein generally refers to any polyribonucleotide or polydeoxyribonucleotide, which may be unmodified RNA or DNA or modified RNA or DNA. Polynucleotide(s) include, without limitation, single- and double-stranded DNA, DNA that is a mixture of single- and double-stranded regions or single- and triple-stranded regions, single- and double-stranded RNA, and RNA that is a mixture of single- and double-stranded regions, hybrid molecules comprising DNA and RNA that can be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as the term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as used herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "polypeptide(s)" as used herein refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides can contain amino acids other than the 20 gene encoded amino acids. "Polypeptide(s)" include those modified either by natural processes, such as processing and other post-translational modifications, but also by chemical modification techniques. Such modifications are well described in research literature, and are well known to those skilled in the art. It will be appreciated that the same type of modification can be present at the same or varying degrees at several sites in a given polypeptide. Also, a given polypeptide can contain many types of modification. Modification can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or a nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation or glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2$^{nd}$ Ed., T. E. Creighton, W. H. Freeman and Company, New York (1993) and Wold, F., Posttranslational Protein Modifications: Perspectives and Prospects. pgs 1-12 in *POSTTRANSLATIONAL COVALENT MODIFICATION OF PROTEINS*, B. C. Johnson. Ed., Academic Press, New York (1983); Seifter et al., *Meth. Enzymol.* 182:626-646 (1990) and Rattan et al., *Protein Synthesis: posttranslational Modifications and Aging*, Ann. N.Y. Acad. Sci. 663: 48-62 (1992). Polypeptides can be branched, or cyclic, with or without branching. Cyclic, branched and non-branched polypeptides can result from post-translational natural processes and can be made by entirely synthetic methods as well.

Preferably, at least a portion of the polypeptide comprises at least 66% identity to the sequence shown in SEQ.ID NO.1. More preferably, a least a portion of the polypeptide comprises at least 83% identity to the sequence shown in SEQ.ID NO.1.

Identity, as used herein, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "identity" and "similarity" can be readily calculated by known methods, including but not limited to those described in (*Computational Molecular Biology*, Lesk, A. M., ed., Oxford University Press, New York, 1988; *Biocomputing: Informatics and genome Projects*, Smith, D. W., ed., Academic Press, New York. 1993; *Computer Analysis of sequence Data*, Part I, Griffin, A. M., and Griffin, H. G., eds., Humana Press. New jersey, 1994; *sequence Analysis in Molecular Biology*, von Heinje, G., Academic Press, 1987; and *sequence Analysis Primer*, Gribskov, M. and Devereux, J., eds., M Stockton Press, New York, 1991; and Carillo, H., and Lipman, D., SIAM *J. Applied Math.*, 48:1073 (1998). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990). The BLAST X program is publicly available from NCBI and other sources (*BLAST Manual*, Altschul, S., et al., NCBI NLM NUH Bethesda, Md. 20894; Altschul, S., et al., *J. Mol Biol.* 215: 403-410 (1990).

Parameters for polypeptide sequence comparison include the following:
 Algorithm: Needleman and Wunsch, J. Mol Biol. 48:443-453 (1970)
 Comparison matrix: BLOSSUM62 from Hentikoff & Hentikoff, Proc. Natl. Acad. Sci. USA. 89:10915-10919 (1992)
 Gap Penalty: 12
 Gap Length Penalty: 4

A program useful with these parameters is publicly available as the "gap" program from Genetics Computer Group, Madison Wis. The aforementioned parameters are the default parameters for peptide comparison (along with no penalty for end gaps). In all cases where a computer program that does not necessarily give the maximized alignment discussed above is used to determine a measure of identity, the default parameters are preferred. Parameters for polynucleotide comparison include the following:
Algorithm; Needleman and Wunsch, J. Mol Biol. 48: 443-453 (1970)
 Comparison matrix: matches=+10, mismatch=0
 Gap Penalty: 50
 Gap Length Penalty: 3

Preferably, the sequence shown in SEQ ID NO. 1, or variants thereof, occurs at the C-terminus of the polypeptide.

Preferably, the polypeptide lacks exon 8. This will result in a polypeptide either lacking or having altered mitotic signalling compared to polypeptides containing exon 8.

A further aspect of the invention provides an isolated polypeptide having anti-angiogenic activity, the polypeptide comprising the sequence shown in SEQ. ID NO. 3, and variants thereof.

A further aspect of the invention provides a nucleotide sequence capable of encoding a polypeptide according to a first or second aspect of the invention.

A further aspect of the invention provides an isolated nucleotide sequence encoding a polypeptide having anti-angiogenic activity, the nucleotide sequence comprising the sequence shown in SEQ.ID NO.2, or variants thereof.

A further aspect of the present invention provides an isolated nucleotide sequence encoding a polypeptide having anti-angiogenic activity, the nucleotide sequence comprising the sequence shown in SEQ. ID NO. 4, or variants thereof.

A further aspect of the present invention provides a polynucleotide comprising a nucleotide sequence that hybridises, particularly under stringent conditions, to a $VEGF_{165}b$ nucleotide sequence, such as the nucleotide sequence shown in SEQ. 2.

As used herein the term "stringent conditions" means hybridisation occurring only if there is at least 83% identity between the sequences. A specific example of stringent hybridisation conditions is overnight incubation at 42° C. in a solution comprising: 50% formamide. 5×SSC (150 mM NaCl, 15 mM trisodium citrate), 50 mM sodium phosphate (pH 7.6), 5× Denhardt's solution, 10% dextran sulphate, and 20 micrograms/ml of denatured, sheared salmon sperm DNA, followed by washing the hybridisation support in 0.1×SSC at about 65° C. Hybridisation and wash conditions are well known and exemplified in Sambrook, et al., Molecular Cloning: A Laboratory Manual, Third Edition, Cold Spring Harbour, N.Y., (1989), particularly Chapter II therein. Solution hybridisation can also be used with the polynucleotide sequences provided by the invention.

A nucleotide sequence according to the invention may be used as a hybridisation probe for RNA, cDNA and genomic DNA to isolate full-length cDNAs and genomic clones encoding $VEGF_{165}b$ and to isolate cDNA and genomic clones of other genes that have a high identity, particularly high sequence identity, to the $VEGF_{165}b$ gene. Such probes will generally comprise at least 15 nucleotide residues or base pairs, and can have at least 18 nucleotide residues or base pairs.

Preferably, the polypeptide and nucleotide sequence of the present invention is a mammalian sequence, such as a primate, rodent, bovine or porcine sequence. More preferably, the sequence is derived from a human sequence. The nucleotide sequence may include, for example, unprocessed RNAs, ribozyme RNAs, hair-pin RNAs for use as interference RNAs, small interfering RNAs (siRNAs), mRNAs, cDNAs, genomic DNAs, B-DNAs, E-DNAs and Z-DNAs.

For recombinant production of the polypeptides of the invention, host cells can be genetically engineered to incorporate expression systems or portions thereof or polynucleotides of the invention. Introduction of a polynucleotide into a host cell may be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbour Laboratory Press, Cold Spring Harbour. N.Y. (1989), such as, calcium phosphate transfection, DEAE-dextran mediated transfection, transfection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli*, streptomyces, cyanobacteria, *Bacillus subtilis*; fungal cells, such as yeast, *Kluveromyces, Saccharomyces*, a basidiomycete, *Candida albicans* and *Aspergillus*; insect cells such as *Drosophila* S2 and *Spodoptera* Sf9; animal cells such as CHO, COS, HeLa, C127, 3T3, BHK, 293, CV-1 and Bowes melanoma cells; and plant cells.

A great variety of expression systems can be used to produce the polypeptides of the invention. Such vectors include, among others, chromosomal-, episomal- and viral-derived vectors, for example, vectors derived from plasmids, from bacteriophage, from transposons, from yeast episomes, from insertion elements, from yeast chromosomal elements, from viruses such as baculoviruses, papova viruses, such as SV40, vaccinia viruses, adenoviruses, adeno-associated viruses, fowl pox viruses, pseudorabies viruses, picornaviruses and retroviruses, and vectors derived from combinations thereof, such as those derived from plasmid and bacteriophage genetic elements, such as cosmids and phagemids. The expression system constructs can contain control regions that regulate as well as engender expression. Generally, any system or vector suitable to maintain, propagate or express polynucleotides or to express a polypeptide in a host can be used for expression in this regard. The appropriate DNA sequence can be inserted into the expression system by any of a variety of well-known and routine techniques, such as, for example, those set forth in Sambrook, et al., *MOLECULAR CLONING: A LABORATORY MANUAL*, (supra).

For secretion of a translated protein into the lumen of the endoplasmic reticulum, into the periplasmic space or into the extracellular environment, appropriate secretion signals can be incorporated into the expressed polypeptide. These signals can be endogenous to the polypeptide or they can be heterologous signals.

Polypeptides of the invention can be recovered and purified from recombinant cell cultures by well-known methods, including ammonium sulphate or ethanol precipitation, extraction such as acid extraction, anion or cation exchange chromatography, gel filtration, phosphocellulose chromatography, hydrophobic interaction chromatography, affinity chromatography, hydroxylapatite chromatography, lectin chromatography, preparative electrophoresis, FPLC (Pharmacia, Uppsala, Sweden), HPLC (e.g., using gel filtration, reverse-phase or mildly hydrophobic columns). Most preferably, high performance liquid chromatography is employed for purification. Well known techniques for refolding proteins can be employed to regenerate an active conformation after denaturation of the polypeptide during isolation and/or purification. In vitro activity assays for polypeptides according to the present invention include, tyrosine kinase receptor activation assays, endothelial cell proliferation (e.g. thymidine incorporation, cell number or BrDU incorporation), cell migration assays (including scratch assays), tube formation, gel invasion assays or pressure or wire myograph assays. In vivo assays include angiogenesis assays using rabbit corneal eye pocket, chick chorioallantoic membrane assays, dorsal skinfold chamber assays, functional blood vessel density, blood flow, blood vessel number, tumour implantation assays (syngeneic or heterogeneic), tumour growth or vessel density assays, growth factor induced assays in hamster cheek pouch, rat, mouse or hamster mesentery, or sponge implant assay (Angiogenesis protcols—Ed. J. Clifford Murray; Humana Press, Totowa, N.J.; ISBN 0-89603-698-7 (part of a Methods in Molecular Medicine series)).

A polypeptide, or polynucleotide comprising a nucleotide sequence, according to the present invention or variants thereof, or cells expressing the same can be used as immunogens to produce antibodies immunospecific for such polypeptides or nucleotide sequences respectively.

A further aspect of the invention provides an isolated VEGF polypeptide or an isolated nucleotide sequence according to a preceding aspect of the present invention for use as an active pharmaceutical substance.

The active pharmaceutical substance is preferably used in the treatment of angiogensis or permeability or vasodilatation-dependent disease conditions as detailed above. Preferably angiogenesis-dependent disease conditions such as tumour growth and metastasis, rheumatoid arthritis, atherosclerosis, neointimal hyperplasia, diabetic retinopathy and other complications of diabetes, trachoma, retrolental fibroplasia, neovascular glaucoma, age-related macular degeneration, trachoma, haemangioma, immune rejection of transplanted corneal tissue, corneal angiogenesis associated with ocular injury or infection, vascular disease, obesity, psoriasis, arthritis, gingivitis and pre-eclampsia.

A further aspect of the invention provides a use of an isolated VEGF polypeptide sequence or an isolated nucleotide sequence according to preceding aspects of the present invention for the preparation of a pharmaceutical composition for the treatment of angiogenesis-dependent disease conditions such as previously mentioned.

A further aspect of the invention provides a method for treating or preventing angiogenesis in a mammalian patient, comprising supplying to the patient a polypeptide comprising the sequence of a VEGF polypeptide according to a previous aspect of the invention.

Preferably, an isolated VEGF polypeptide according to a previous aspect of the invention is capable of heterodimerising with endogenous VEGF thereby preventing or reducing VEGF-mediated cell proliferation or by direct binding to receptor normally the ligand for endogenous VEGF.

A further aspect of the invention provides a method for treating or preventing angiogenesis in a mammalian patient, comprising supplying to the patient a polynucleotide comprising a nucleotide sequence according to a previous aspect of the invention.

A further aspect of the invention provides a method for preventing or reducing VEGF-mediated cell proliferation in a mammalian patient comprising supplying to the patient a polypeptide comprising the sequence of an isolated VEGF polypeptide according to a previous aspect of the invention.

A further aspect of the invention provides a method for preventing or reducing VEGF-mediated cell proliferation in a mammalian patient comprising supplying to the patient a polynucleotide comprising the sequence of an isolated nucleotide sequence according to a previous aspect of the invention.

A further aspect of the invention provides a method for preventing or reducing $VEGF_{165}$-mediated vasodilatation in a mammalian patient comprising supplying to the patient a polypeptide comprising the sequence of a VEGF polypeptide according to a previous aspect of the invention.

A further aspect of the invention provides a polypeptide comprising the sequence of a VEGF polypeptide according to a preceding aspect of the invention for use in the treatment of $VEGF_{165}$-mediated vasodilatation.

A further aspect of the invention provides a use of a polypeptide comprising the sequence of a VEGF polypeptide according to a preceding aspect of the invention for the preparation of a pharmaceutical composition for the treatment of $VEGF_{165}$-mediated vasodilatation.

A further aspect of the invention provides a method for preventing or reducing $VEGF_{165}$-mediated vasodilatation in a mammalian patient comprising supplying to the patient a polynucleotide comprising the sequence of an isolated nucleotide according to a preceding aspect of the invention.

A further aspect of the invention provides a polynucleotide comprising the sequence of a nucleotide according to a previous aspect of the invention for use in the treatment of $VEGF_{165}$-mediated vasodilatation. Conditions in which $VEGF_{165}$-mediated vasodilatation is observed include, for example, cancer, psoriasis, arthritis etc.

A further aspect of the invention provides a use of a polynucleotide comprising a nucleotide sequence according to a preceding aspect of the invention in the preparation of a pharmaceutical composition for the treatment of $VEGF_{165}$-mediated vasodilatation.

A further aspect of the invention provides a pharmaceutical composition comprising a polypeptide comprising the sequence of a VEGF polypeptide according to a previous aspect of the invention and a pharmaceutically acceptable diluent.

Preferably, the vasodilatation and/or angiogenesis is associated with hair growth, as seen, for example, in hirsuitism. Any reduction in vasodilatation and/or angiogenesis would result in hair loss (Yano et al J Clin Invest (2001), 107 409-17).

A further aspect of the invention provides a pharmaceutical composition comprising a polynucleotide comprising a nucleotide sequence according to a previous aspect of the invention and a pharmaceutically acceptable diluent.

A further aspect of the invention provides an antibody raised against a VEGF polypeptide or nucleotide sequence according to a previous aspect of the invention.

Antibodies generated against the polypeptides or polynucleotides of the invention can be obtained by administering the polypeptides or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in MONOCOLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms such as other mammals, can be used to express humanized antibodies immunospecific to the polypeptides or polynucleotides of the invention.

Alternatively, phage display technology can be utilized to select antibody genes with binding activities towards a polypeptide of the invention either from repertoires of PCR amplified v-genes of lymphocytes from humans screened for possessing anti-$VEGF_{165}$b or from libraries (McCafferty, et al., (1990), Nature 348, 552-554; Marks, et al., (1992) Biotechnology 10, 779-783). The affinity of these antibodies can also be improved by, for example, chain shuffling (Clackson et al., (1991) Nature 352:628).

The above-described antibodies can be employed to isolate or to identify clones expressing the polypeptides or polynucleotides of the invention to purify the polypeptides or polynucleotides by, for example, affinity chromatography.

The polynucleotides, polypeptides and antibodies that bind to or interact with a polypeptide of the present invention can also be used to configure screening methods for detecting the effect of added compounds on the production of mRNA or polypeptide in cells. For example, an ELISA assay can be constructed for measuring secreted or cell associated levels of polypeptide using monoclonal and polyclonal antibodies by standard methods known in the art. This can be used to discover agents which can inhibit or enhance the production of polypeptide (also called antagonist or agonist, respectively) from suitably manipulated cells or tissues.

The invention also provides a method of screening compounds to identify those which enhance (agonist) or block (antagonist) the anti-angiogenic action of $VEGF_{165}b$ polypeptides or polynucleotides. The method of screening can involve high-throughput techniques. For example, to screen for agonists or antagonists, a synthetic reaction mix, a cellular compartment, such as a membrane, cell envelope or cell wall, or a preparation of any thereof, comprising $VEGF_{165}b$ polypeptide and a labelled substrate or ligand of such polypeptide is incubated in the absence or the presence of a candidate molecule that may be a $VEGF_{165}b$ agonist or antagonist. The ability of the candidate molecule to agonize or antagonize the $VEGF_{165}b$ polypeptide is reflected in decreased binding of the labelled ligand or decreased production of product from such substrate. Molecules that bind gratuitously, i.e., without inducing the anti-angiogenic effects of $VEGF_{165}b$ polypeptide are most likely to be good antagonists. Molecules that bind well and increase the anti-angiogenic effects of $VEGF_{165}b$ are agonists. Detection of the increase in anti-angiogenic action can be enhanced by using a reporter system. Reporter systems that can be useful in this regard include but are not limited to colorimetric, labelled substrate converted into product, a reporter gene that is responsive to changes in $VEGF_{165}b$ polynucleotide or polypeptide activity, and binding assays known in the art.

The invention further provides an inhibitor of a VEGF polypeptide according to a preceding aspect of the invention, for use in the treatment of vasoconstriction.

As pre-eclampsia results from poor placental invasion, i.e. a failure of angiogenesis, and VEGF antibodies have been shown to block the cause of hypertension in pre-eclampsia (Brockelsby et al Lab Invest 1999; 79:1101-11) this is considered by the present inventors to be potentially caused by excess new variant $VEGF_{165}b$, and thus inhibition of this new variant $VEGF_{165}b$, is expected to provide a treatment for pre-eclampsia.

It is presently believed that the inhibitor is capable of binding endogenous $VEGF_{165}b$, thereby preventing or reducing $VEGF_{165}b$-mediated vasoconstriction where vasoconstriction is associated with pre-eclampsia, and thus may be due to excess $VEGF_{165}b$ expression.

The inhibitor may comprise an antibody according to a preceding aspect of the invention, for example, the inhibitor may be an exon 9 specific neutralising antibody.

Alternatively, the inhibitor may be a polynucleotide having a complementary sequence to the sequence of an isolated polynucleotide according to a previous aspect of the invention.

Inhibitors or $VEGF_{165}b$ may be identified in suitable screens in which a candidate compound is screened for its ability to inhibit $VEGF_{165}b$. Such screens may be carried out in respect of a plurality of compounds, for example, from a compound library.

An inhibitor identified using such a screen may be synthesised and formulated into a pharmaceutical composition for use.

The present invention also provides a method for preventing or reducing vasoconstriction in a mammalian patient comprising supplying to the patient an inhibitor according to a preceding aspect of the invention.

The present invention also provides a use of an inhibitor according to a previous aspect of the invention for the preparation of a pharmaceutical composition for the treatment of vasoconstriction.

The invention also provides an assay for the specific detection of $VEGF_{165}b$ in a sample comprising carrying out a polymerase chain reaction on at least a portion of the sample, using an annealing temperature of at least 59° C. and the following primer sequences:

```
exon 4 (forward primer):
GAGATGAGCTTCCTACAGCAC           (SEQ ID NO: 1)

9H (reverse primer):
TTAAGCTTTCAGTCTTTCCTGGTGAGAGATCTGCA  (SEQ ID NO: 2)
``` or variants thereof, wherein the variants retain the same annealing properties with respect to the $VEGF_{165}b$ nucleotide sequence as the above primers.

This method allows the specific detection of $VEGF_{165}b$ in a sample, even when the sample contains both $VEGF_{165}b$ and $VEGF_{165}$.

Preferably, an annealing temperature of 60° C. is used.

Preferably, the method can detect $VEGF_{165}b$ in a sample containing $VEGF_{165}$ at a concentration of up to 100 times greater, and preferably up to 500 times greater, more preferably 1000 times greater than the concentration of $VEGF_{165}b$ in the sample.

A further aspect of the invention provides an isolated VEGF nucleotide sequence according to the present invention for use in the detection of exon 9 containing VEGF isoforms by quantitative real-time PCR. A number of technologies are available and known to those skilled in the art, these technologies would for example include but not be limited to: Taqman, Scorpion, Molecular Beacon (FRET).

In preceding aspects of the invention, $VEGF_{165}b$ or its inhibitor is preferably supplied to a patient by injection. Preferably, VEGF is supplied to a patient by intra-arterial, intravenous, intramuscular, intra-peritoneal or subcutaneous injection. However when local application is required a regional injection may be preferable, and this can be inferred from the site of the disease process eg intra-articular or intraorbital injection. Alternatively, $VEGF_{165}b$ or inhibitor thereof may be supplied orally or topically. For example, in the treatment of gingivitis, $VEGF_{165}b$ could be supplied orally in the form of a toothpaste or mouthwash containing $VEGF_{165}b$. For psoriasis $VEGF_{165}b$ could be contained within an emollient cream, for herpes ocular infection in the form of eye-drops or cream, for pulmonary lesions in a nebulized aerosol.

The combination of $VEGF_{165}b$ with other agents for simultaneous administration to a mammalian patient via any of the aforementioned routes in any clinical situation in which the simultaneous administration may be deemed beneficial in the light of the poperties of $VEGF_{165}b$ and the other agent or agents. Specific combinations of $VEGF_{165}b$ and another agent or agents would be apparent to the skilled person from the particular clinical situation involved. For example, such a combination may be the simultaneous administration in a cream or eyedrop of $VEGF_{165}b$ and acyclovir or similar such agent, for the simultaneous treatment of ocular herpes infection and the corneal angiogenesis that accompanies it. Another such example is the simultaneous administration of $VEGF_{165}b$ and an anti-inflammatory agent via intrarticular injection in rheumatoid disease. Another such example is the simultaneous administration of $VEGF_{165}b$ and a chemo or immunotherapeutic agent to a tumour condition in a patient.

A further aspect of the invention provides an isolated chemical or biological agent that can inhibit a switch of splicing from sequences described in the said invention to previously described sequences. For example, such an inhibitor could be used to prevent the splicing of a sequence to exclude exon 9. For example, the splicing of mRNA to give $VEGF_{165}$ (which includes exon 8 rather than exon 9) instead of $VEGF_{165b}$ (which contains exon 9 rather than exon 8) could be prevented. This would allow the treatment of $VEGF_{165}$-mediated conditions by supplying to a patient the agent that inhibits the switch in splicing from $VEGF_{165b}$ to $VEGF_{165}$.

Embodiments of the present invention will now be described, by way of example only, and with reference to the following figures, in which:

FIG. 1 is a diagram showing the mRNA splicing and structure of the VEGF pre-mRNA and positions of relevant PCR primers EX7a, Ex7b, 3'UTR, V165K and V165X. Exon 7a and 3' UTR primers were designed to amplify a 164 by sequence if VEGF148 was present, 133bp if VEGF 165b was present, a 199 bp product if longer splice variants were present, and no band if shorter variants were present. V165K and V165X were designed to amplify to full length product. VEGF165b would result in a 663 bp product, VEGF165a 729 bp product, VEGF189 an 801 bp product and VEGF206 a 852 bp product. Exon 7b and 3 UTR were designed to amplify only products from longer splice variants (2165) but no product from VEGF148.

FIGS. 2A and 2B are photographs of agarose gels containing bands corresponding to PCR products. In FIG. 2A, primers used were 7b and 3'UTR. In FIG. 2B, primers used were 7a and 3'UTR.

FIG. 3A is a photograph of an agarose gel showing the PCR products obtained using exon 7a primer and 3' UTR primer and mRNA templates obtained from the opposite poles of four human nephrectomy specimens, FIG. 3A shows a PCR of cDNA reverse transcribed from mRNA extracted from four paired renal tissues. Bands were seen at ~150 bp ($VEGF_{155b}$) in all four benign samples (B1-B4) and two of the malignant tissues (M3-M4), but not in two malignant tissues (M1-M2). Bands were cloned and sequenced from B1-4 and M4).

FIG. 4A is the nucleotide sequence of $VEGF_{165}$ (SEQ ID NO:19) and $VEGF_{165}b$ (SEQ ID NO:27) cDNA. The 66 bp downstream of exon 7 are missing from $VEGF_{165}b$.

FIG. 4B is the exon structure of the C-terminal end of $VEGF_{165}$ and $VEGF_{165}b$. The 3' UTR sequence of exon 8 contains a consensus intronic sequence for exon 9, a CT rich region and a CAG immediately prior to the splice site. The nucleotide sequence results in an alternate 6 amino acid C terminus. Capital letters are open reading frames, lower case introns or 3'UTR (italics, $VEGF_{165}$, bold, $VEGF_{165}b$). (SEQ ID NOS:20, 28, 29, 31 &30 are disclosed respectively in order of appearance).

FIG. 4C is the predicted amino acid sequence of $VEGF_{165}$ (SEQ ID NO:20) compared to $VEGF_{165}b$ (SEQ ID NO:31). The 6 alternative amino acids result in a different C-terminal structure of the VEGF likely to affect receptor activation, but not receptor binding or dimerisation. The Cys is replaced with a Ser and the C terminal amino acids are a basic (underlined) and an acidic (italics) moiety instead of two acidic ones. Therefore the net charge on this end of the molecule will be altered.

Figures 5A, 5B:
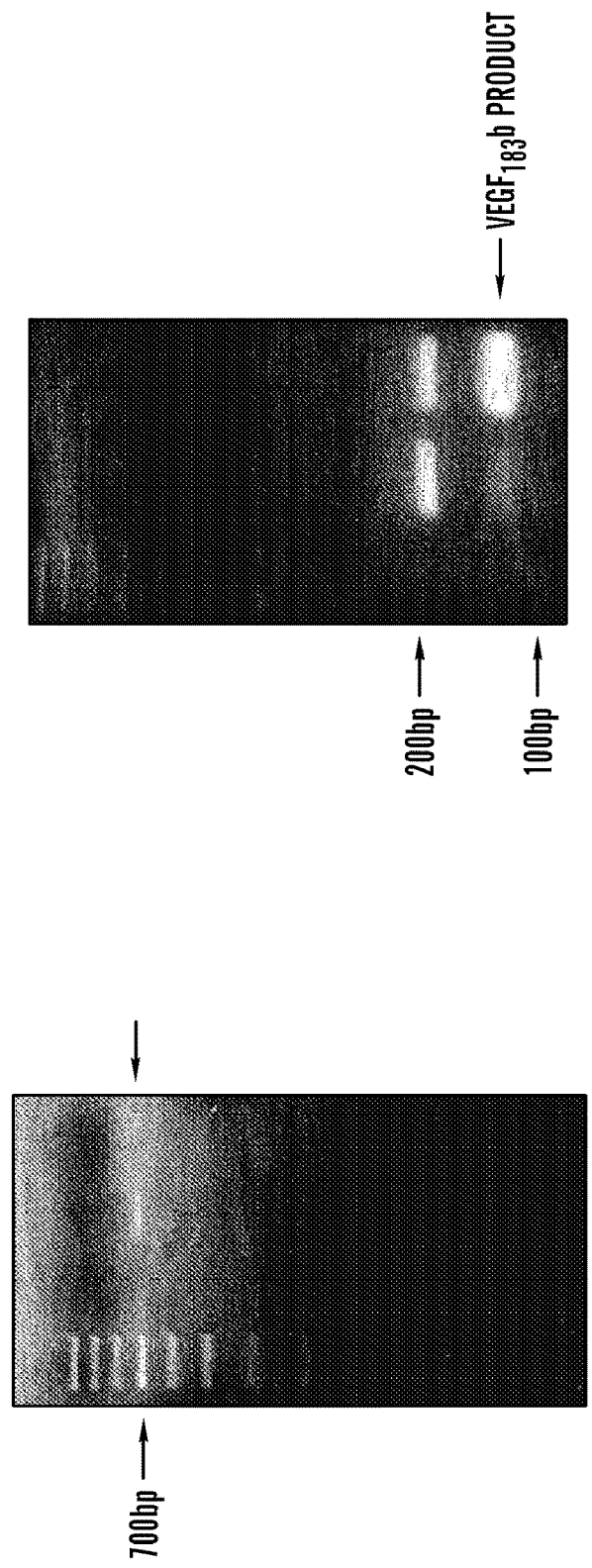

FIG. 5A is an agarose gel showing the ~700 bp PCR product of V165K and V165X. The SDS page gel shows the ~700 bp PCR product of V165K and V165X excised from agarose gel and purified.

FIG. 5B is an SDS gel showing the products of the nested PCR using the excised band as a template and exon 7 and 3'UTR as primer pairs.

Figures 6A, 6B:
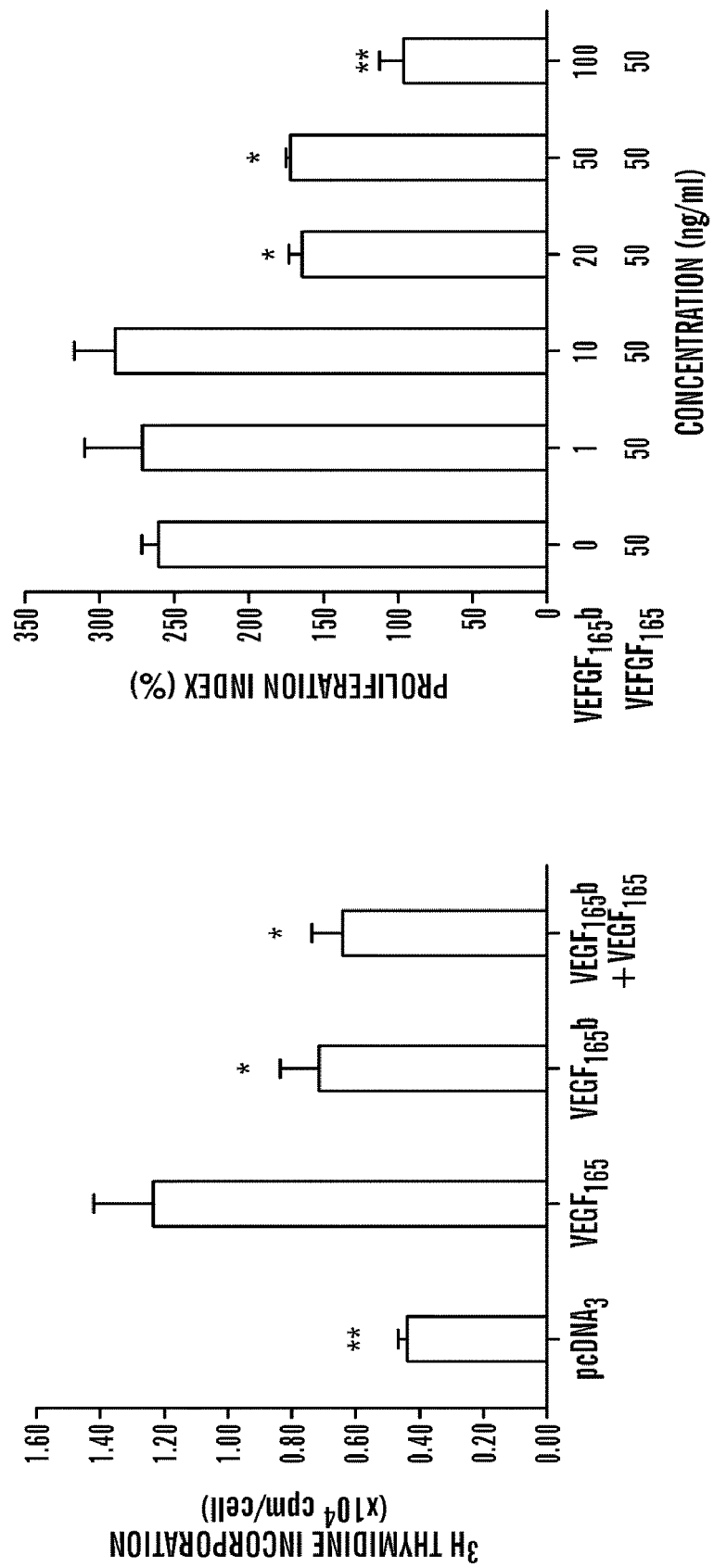

FIGS. 6A-6D show the effect of $VEGF_{165b}$ on HUVEC proliferation. FIG. 6A shows the effect of $VEGF_{165}b$ on $VEGF_{165}$ stimulated HUVEC proliferation. In FIG. 6A $^3H$-thymidine incorporation per cell was assessed in HUVECs incubated with CM without VEGF (pcDNA), 100 ng/ml $VEGF_{165b}$, or 100 ng/ml of both ($VEGF_{165b}$+ $VEGF_{165}$), n=3. p<0.01, ANOVA.

FIG. 6B shows dose response studies of the above effect. In FIG. 6B, proliferation index was measured in HUVEC treated with both isoforms compared to that treated with no $VEGF_{165}$ n=3, p=0.001, ANOVA.

Figure 6C:
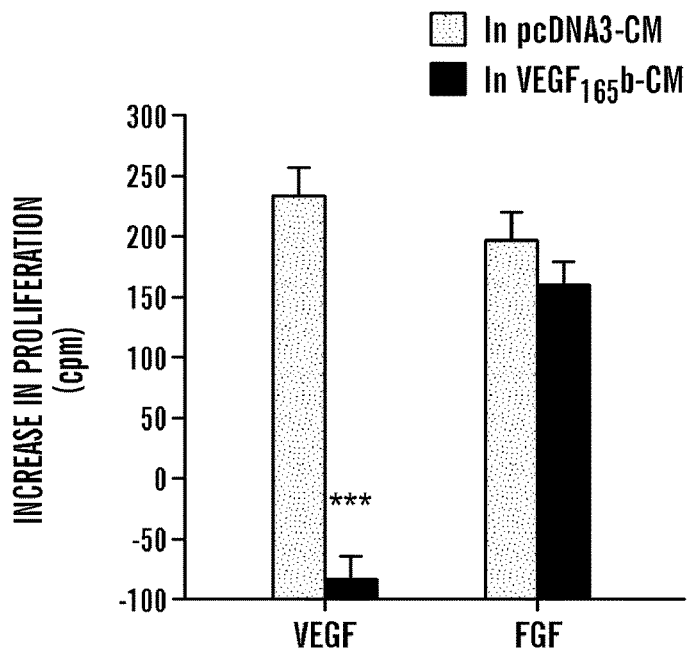

FIG. 6C demonstrates the effect of $VEGF_{165}b$ on $VEGF_{165}$ and FGF stimulated HUVEC $^3H$-thymidine incorporation. In FIG. 6C, $^3H$-thymidine was incorporated in HUVECs incubated with pcDNA3-CM (stippled), or $VEGF_{165b}$, CM (black bars) with 40 ng/ml $VEGF_{165b}$ or 50 ng/ml bFGF, n=3 p<0.01, ANOVA, =p<0.01, *=p<0.001 compared to $VEGF_{165}$.

Figure 6D:
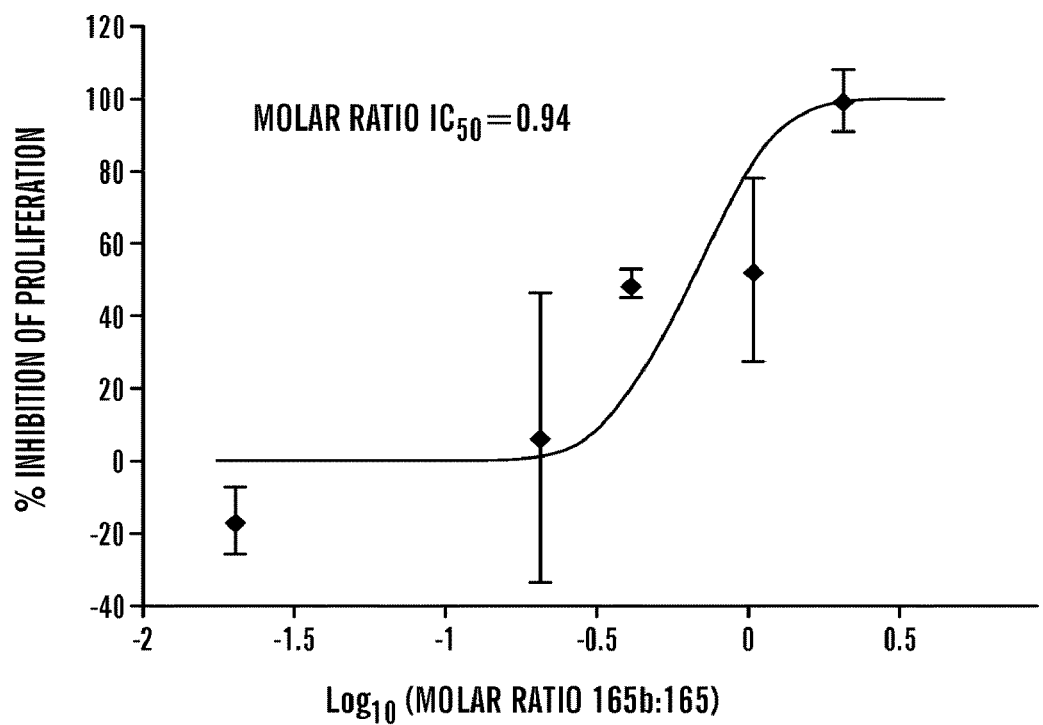

FIG. 6D shows a dose response curve of the inhibition of cell proliferation compared to the log molar ratio of $VEGF_{165}b$ to $VEGF_{165}$.

Figure 7A:
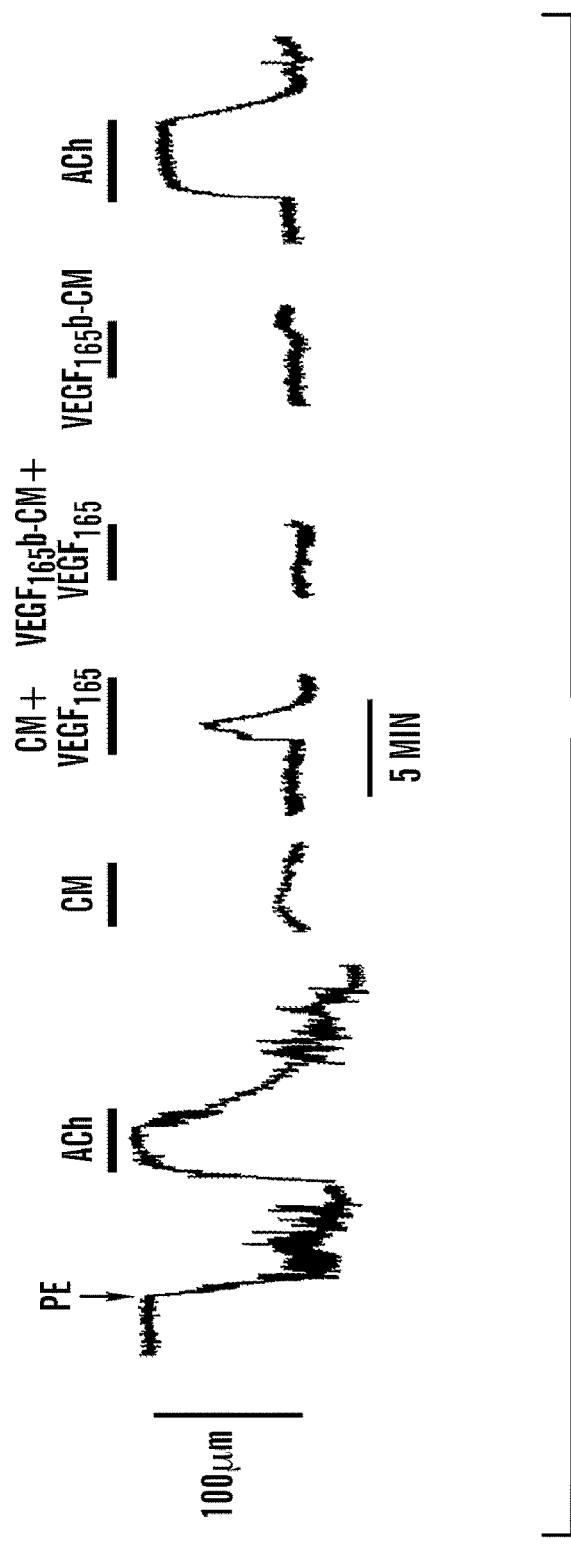
Figure 7B:
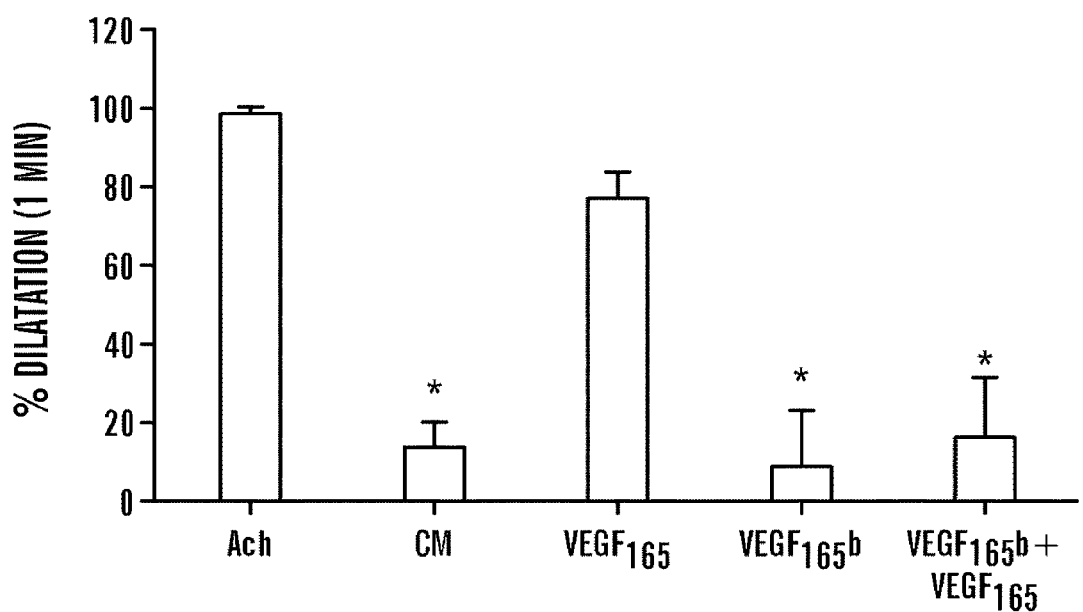

FIGS. 7A and 7B show the effect of $VEGF_{165}$ and $VEGF_{165}b$ on the diameter of rat mesenteric arteries preconstricted with phenylephrine. FIG. 7A shows an example of diameter measurements in a 265 pm diameter mesenteric artery. The vessel was constricted with 1 uM Phenylephrine. When perfused with 10 uM acetylcholine the vessel dilated, demonstrating endothelium dependent tone. Dialyzed pcDNA3-CM (CM) did not affect diameter, whereas 20 ng/ml $VEGF_{165}$ (in CM) caused a robust transient vasodilation. $VEGF_{165b}$-CM (40 ng/ml) $VEGF_{165b}$. FIG. 7B shows mean percent vasodilation for 5 vessels, P<0.01, ANOVA, n=5, *=p<0.05 compared to $VEGF_{165}$ SNK post hoc test. The order of perfusions were varied and there was no dependence of the response on the order of perfusion.

Figure 8:
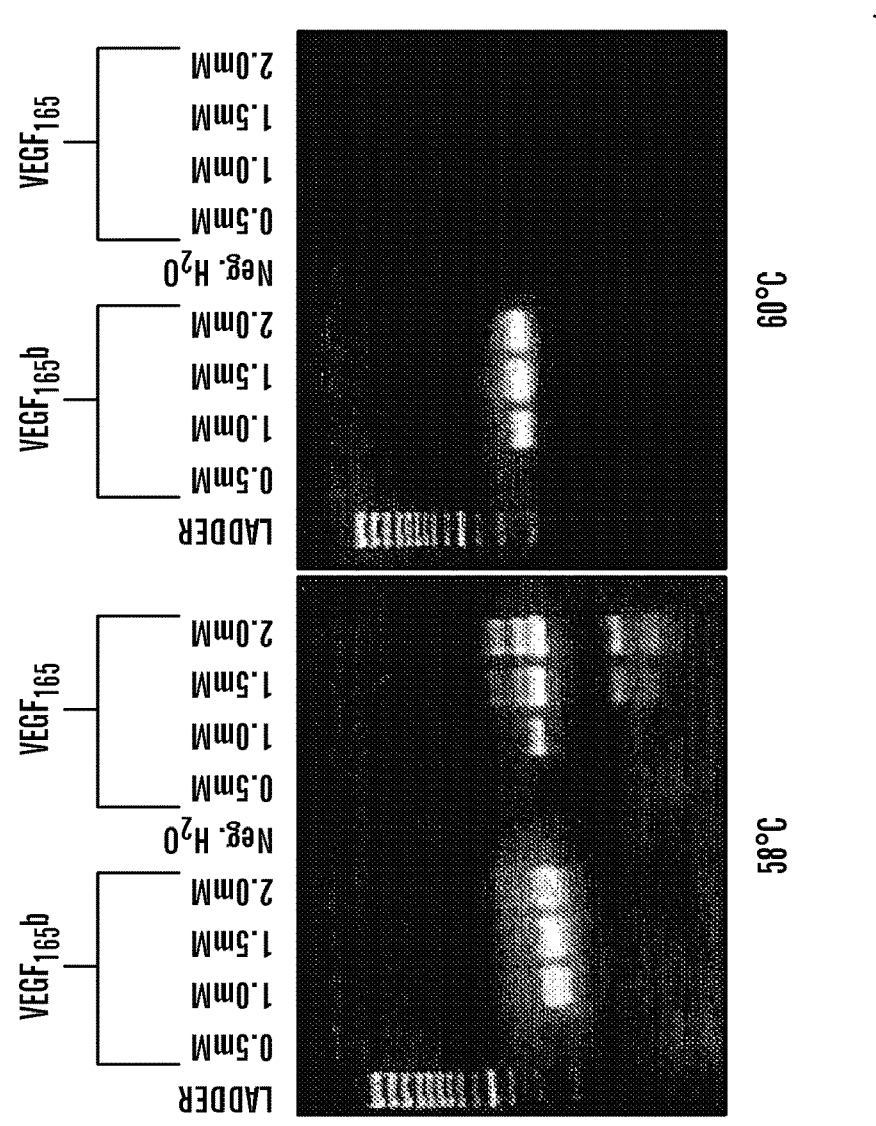
Figure 9A:
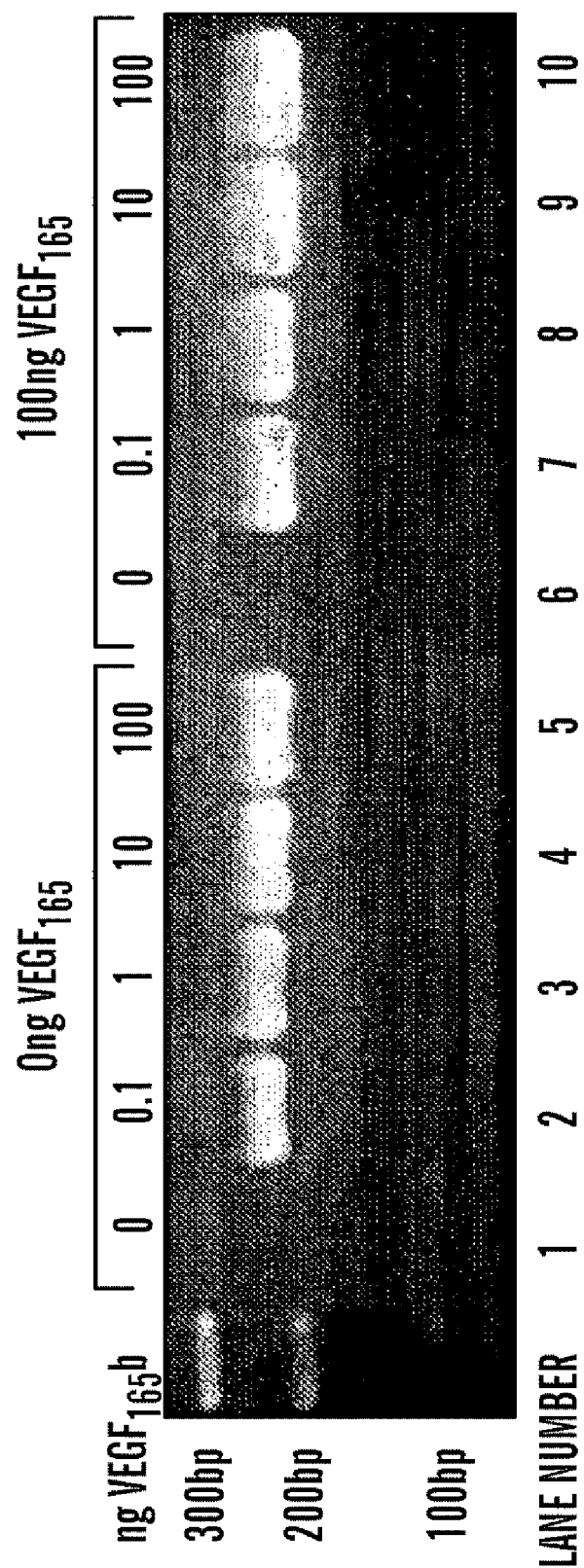
Figure 9B:
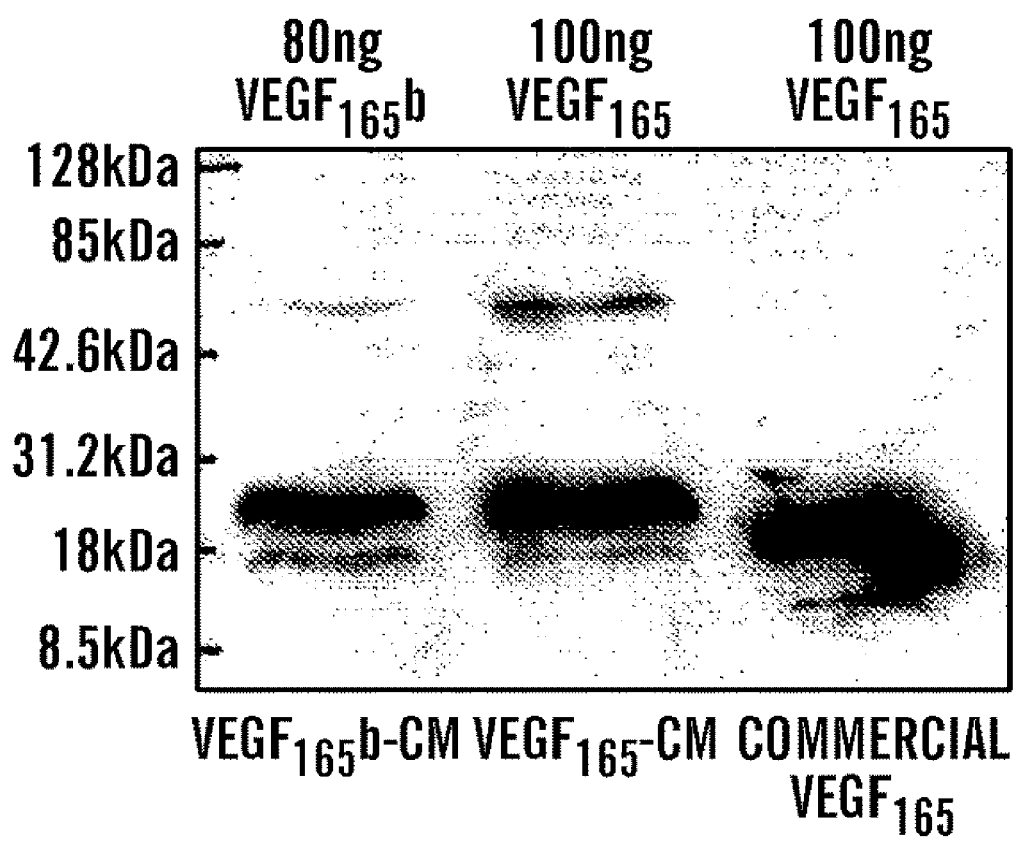

FIG. 8 is a photograph of an agarose gel showing the PCR products obtained using exon 9 specific primers and $VEGF_{165}$ and $VEGF_{165}b$ templates and annealing temperatures of 58° C. and 60° C. and a range of $MgCl_2$ concentrations;

FIGS. 9A-9B show detection of synthetic $VEGF_{165b}$. FIG. 9A is a photograph of an agarose gel showing the PCR products obtained using $VEGF_{165}$ and $VEGF_{165}b$ templates and an annealing temperature of 60° C. in PCR competition assays. Lanes 2 and 6 indicate the reactions in which the primers detected $VEGF_{165}b$ in preference to $VEGF_{165}$ when $VEGF_{165}$ was present at 1000× the concentration of $VEGF_{165}b$. Isoform specific PCR using—exon 9 and exon 4 primers with cloned $VEGF_{165b}$ and $VEGF_{165}$ as template. No amplification was seen in the absence of $VEGF_{165b}$ (lanes 1 & 6) even in the presence of 100 ng $VEGF_{165}$ (lane 6). However, $VEGF_{165b}$ was detected in the absence of (lanes 2-5) or presence of (lanes 7-10) excess $VEGF_{165}$.

FIG. 9B is a photograph of a Western blot showing expression of recombinant $VEGF_{165}b$, $VEGF_{165}$ produced by transfected HEK293 cells and commercial VEGF (Peprotech, NJ, USA). Both isoforms are the same size (~23 kDa) and a small amount of homodimerization occurs.

FIGS. 10A and 10B show photographs of agarose gels containing PCR products of a tissue screen in various tissues using primers which detect exon 8 and exon 9 containing (10A) isoforms and Exon 9 specific isoforms (FIG. 10B).

PCR showing expression of exon 9 containing isoforms in various tissues using specific PCR that only detects exon 9 containing isoforms.

Figure 11:
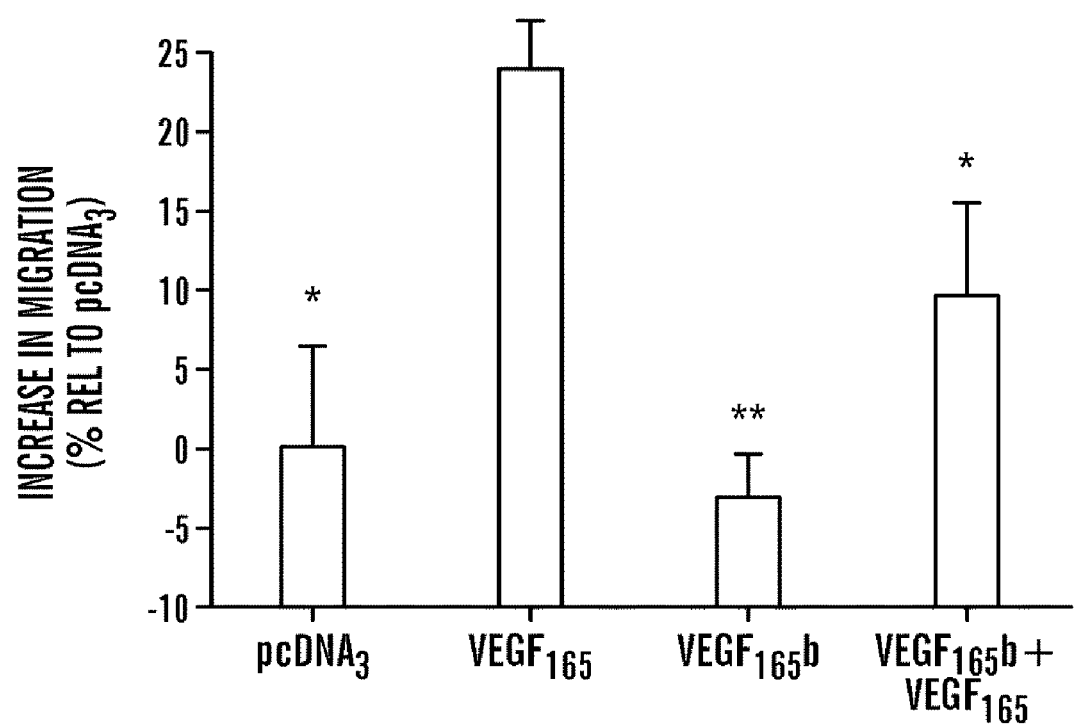

FIG. 11 shows the effect of VEGF$_{165}$b on VEGF$_{165}$-mediated HUVEC migration. Cell migration assessed in HUVECs incubated with pcDNA3-CM (<62.5 pg/ml VEGF), VEGF$_{165}$-CM (33 ng/ml VEGF$_{165}$), VEGF$_{165b}$-CM(33 ng/ml VEGF$_{165b}$), or a combination of both CM (33 ng/ml each VEGF isoform). P<0.01, ANOVA, n=6. *=p<0.05, **=p<0.01 compared to VEGF$_{165}$.

Figure 12B:
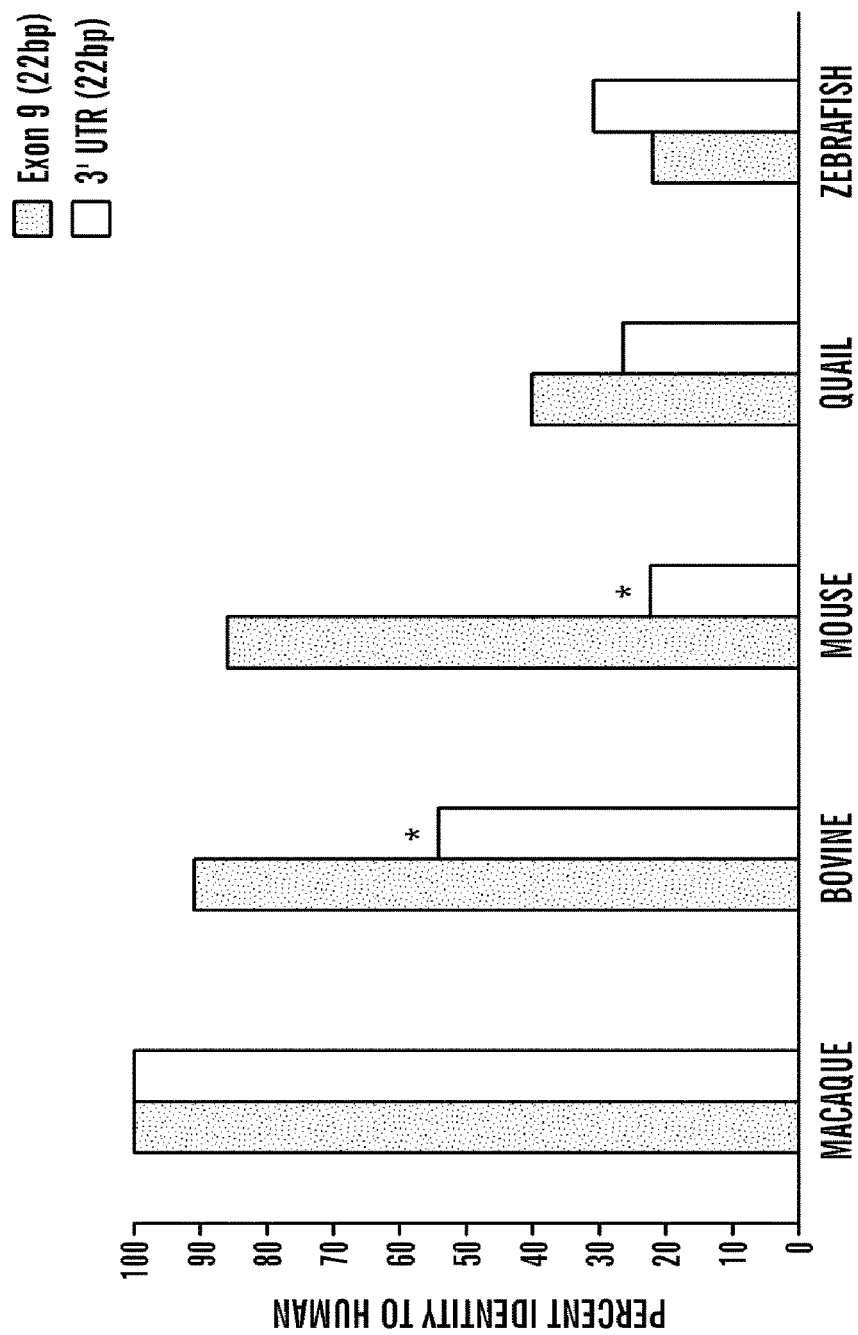

FIGS. 12A-12B summarise the sequence identity of exon 9 in different species (SEQ ID NOS 21-23 are disclosed respectively in order of appearance). Sequence identity of Exon 9 and the sequence immediately downstream of exon 9 between different species. FIG. 12A shows that although there is 90% identity (shaded) between human and bovine exon 9 (italics), there is significantly less identity in the equivalent twenty two 3' base pairs, suggesting that the exon 9 sequence is conserved between species. In the mouse there is a single base pair deletion relative to the human which introduces a frame shift. A second mutation (C$_{mouse}$->T$_{human}$) rescues the stop codon (underlined). FIG. 12B shows a comparison of identity in exon 9 compared to the equivalent number of base pairs immediately 3' in five different species. *=exon 9 is significantly more highly-conserved than the 3'UTR, p<0.01 (X2 test) compared to exon 9.

Figure 13C:
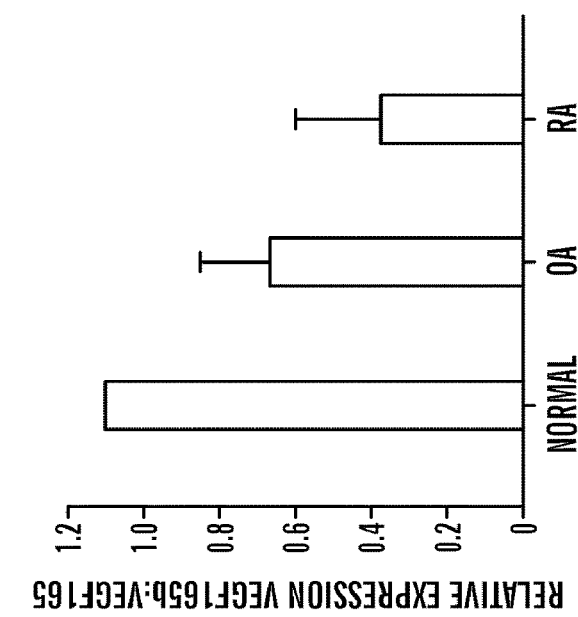
Figure 13A:
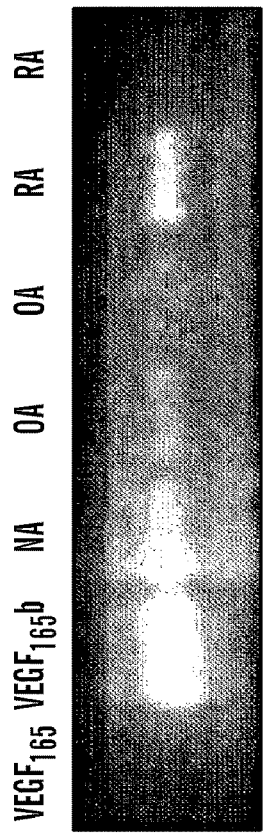
Figure 13B:
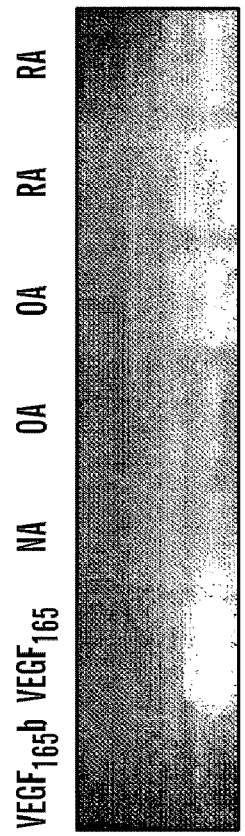

FIGS. 13A-C show PCR products using exon 9 (13a) or exon 8 (13b) specific primers showing VEGF$_{165}$b mRNA expression in normal, osteoarthritic and rheumatoid synovium, and, (13c) their relative expression. In FIG. 13A, a differential mRNA expression of VEGF$_{165b}$ and VEGF$_{165}$ from normal and arthritic synovial tissue. mRNA was isolated from synovium from patients with non-arthritic (NA), rheumatoid arthritis (RA) and osteoarthritis (OA). In FIG. 13B, relative expression of VEGF$_{165b}$:VEGF$_{165}$ mRNA.

Figures 14A, 14B:
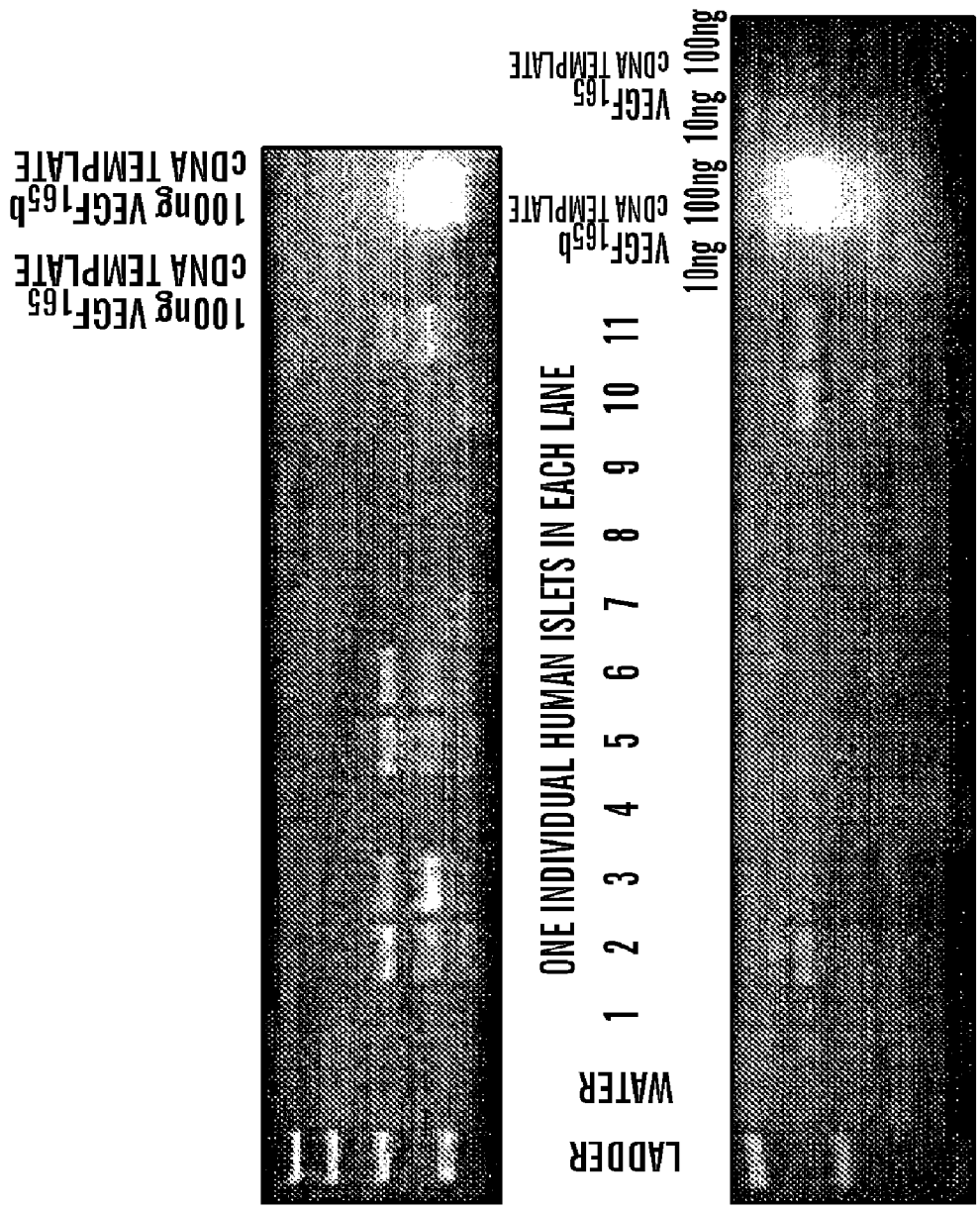

FIGS. 14A and 14B show the expression of exon 8 and exon 9 containing VEGF isoforms in individual human pancreatic islets. Heterogeneity can be seen in exon 8 (upper gel) and exon 9 (lower gel) containing VEGF species in individual human pancreatic islets.

Figure 15A:
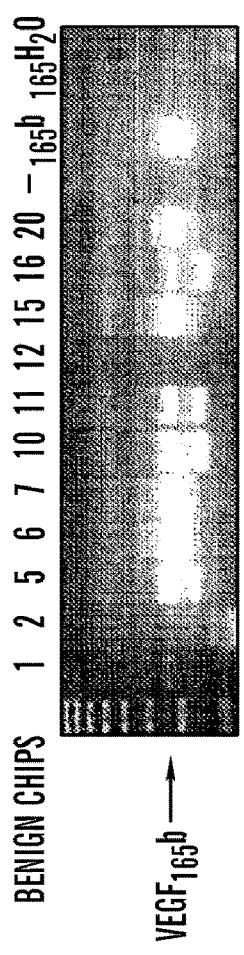
Figure 15B:
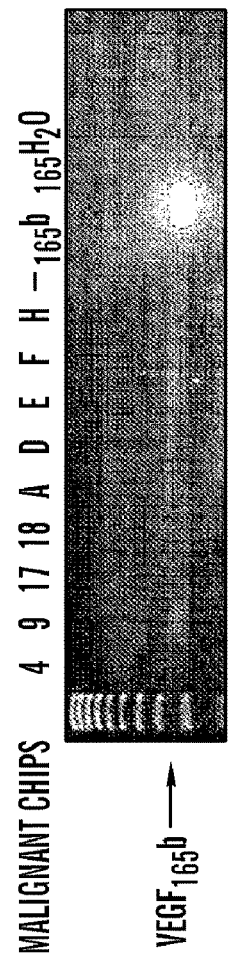
Figure 15C:
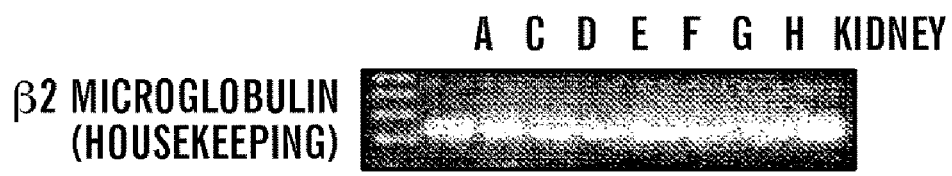
Figure 15D:
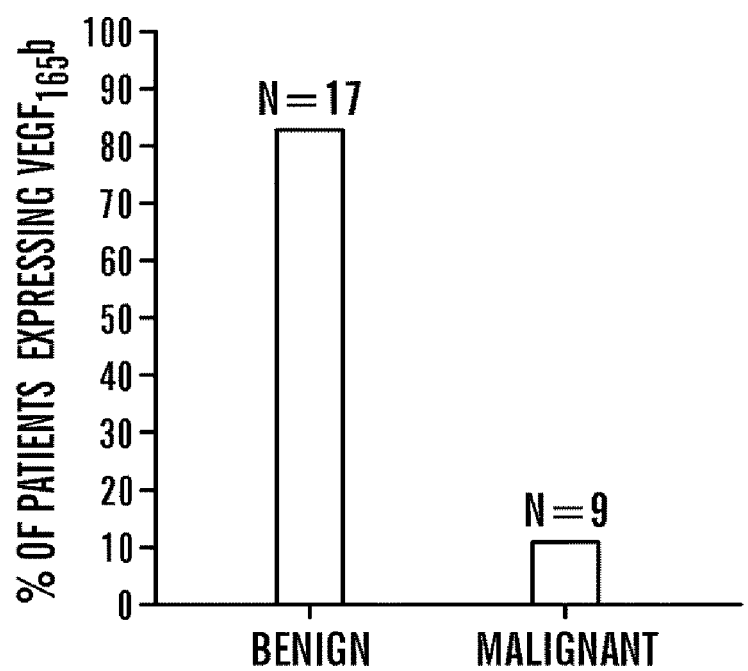

FIGS. 15A-D detail the change in VEGF$_{165}$b expression in malignant versus benign Trans-urethral resection of prostate curettings. Expression of VEGF$_{165b}$ in TURP chips from BPH and MPC mRNA was extracted from the chips and reverse transcribed using standard methodology and amplified using primers specific to VEGF$_{165b}$. FIG. 15A shows an RT-PCR of RNA extracted from benign prostate chips using primers to detect VEGF$_{165b}$. Eleven of the twelve benign samples showed clear expression of VEGF$_{165b}$. VEGF$_{165b}$ positive controls and VEGF$_{165}$ negative controls are also shown. The one sample that did not show expression (sample number 12) was also negative for 13-microglobulin (i.e., no cDNA was present). FIG. 15B shows an RT-PCR of RNA extracted from malignant prostate chips using primers to detect VEGF$_{165b}$. Only one of the nine malignant samples showed clear expression of VEGF$_{165b}$. VEGF$_{165b}$ positive controls, and VEGF$_{165}$ negative controls are also shown. FIG. 15C shows 13-microglobulin expression in the malignant tissues to show that mRNA was effectively purified and reverse transcribed. FIG. 15D shows a percentage of prostates in which TURP chips showed expression of VEGF$_{165b}$ mRNA. P<0.001 (Fisher's Exact Test).

Figure 16A:
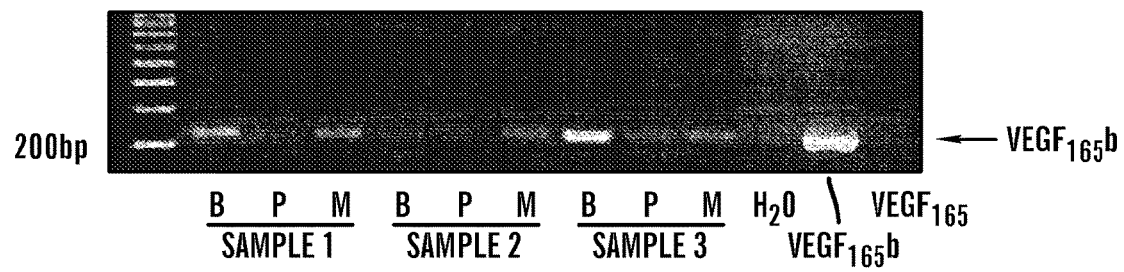
Figure 16B:
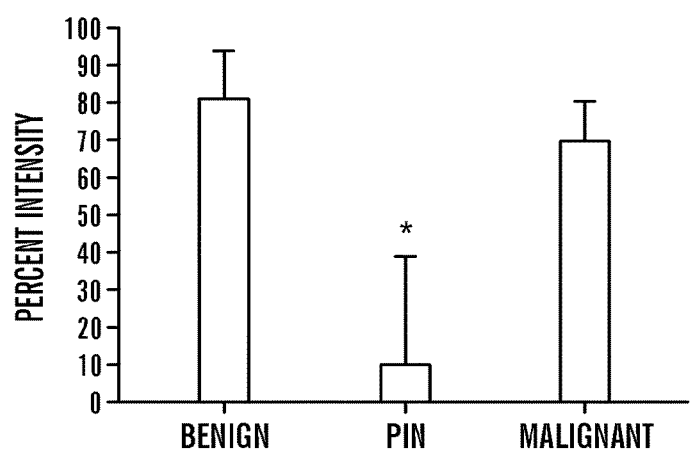

FIG. 16A is a photograph of a gel showing PCR products from archival radical prostatectomy samples. Expression of VEGF$_{165b}$ in sections of paraffin embedded fixed sections of prostate tissue. In FIG. 16A, mRNA was extracted from six 5 um sections of prostate from histologically defined normal (N), prostate intraepithelial neoplasia (P), or frank carcinoma (C) and reverse transcribed using standard methodology and amplified using primers specific to VEGF$_{165b}$. In FIG. 16B, mean ±SEM densities of 15 PCR products measured using image analysis software. Density of bands are expressed as the percentage of the maximum intensity per patient sample.

Figure 17:
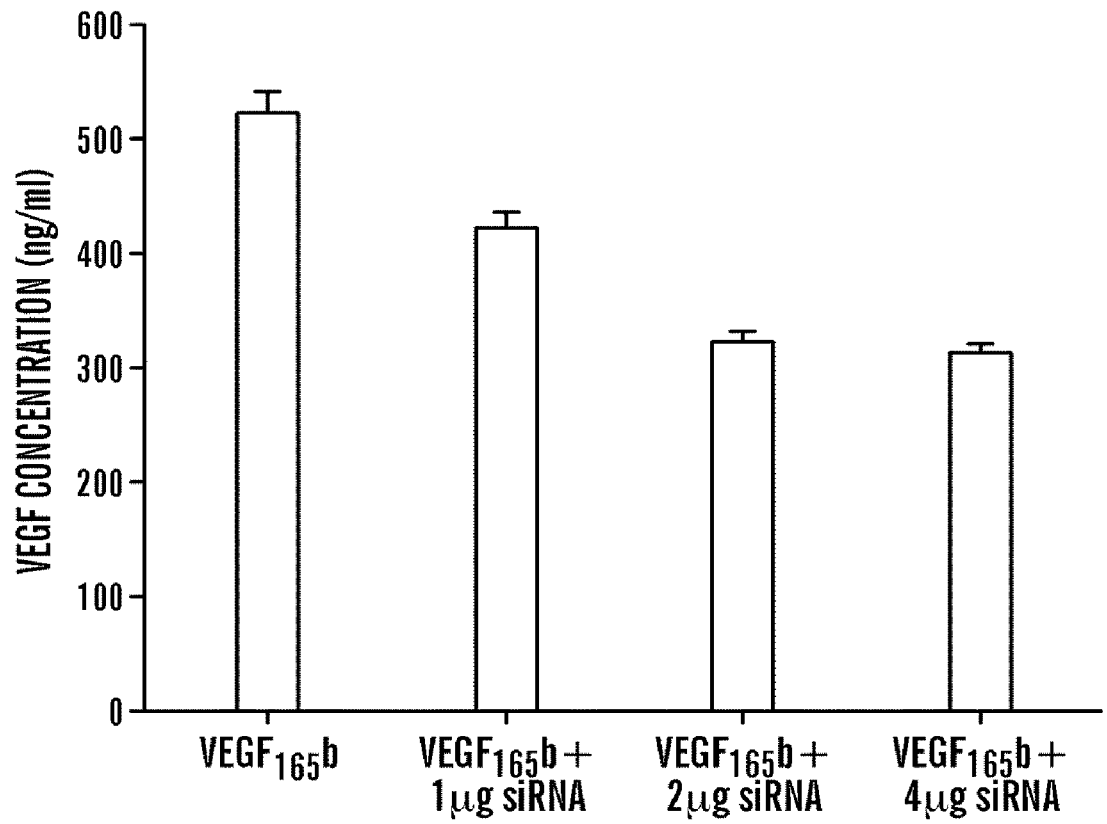

FIG. 17 shows the VEGF concentration in media taken from human embryonic kidney cells (HEK293) transfected with 2 μg VEGF$_{165}$b cDNA (in expression vector pcDNA3) alone or with increasing amounts of double stranded siRNA directed across the exon 7-exon 9 splice site.

EXAMPLE 1

Figure 1:
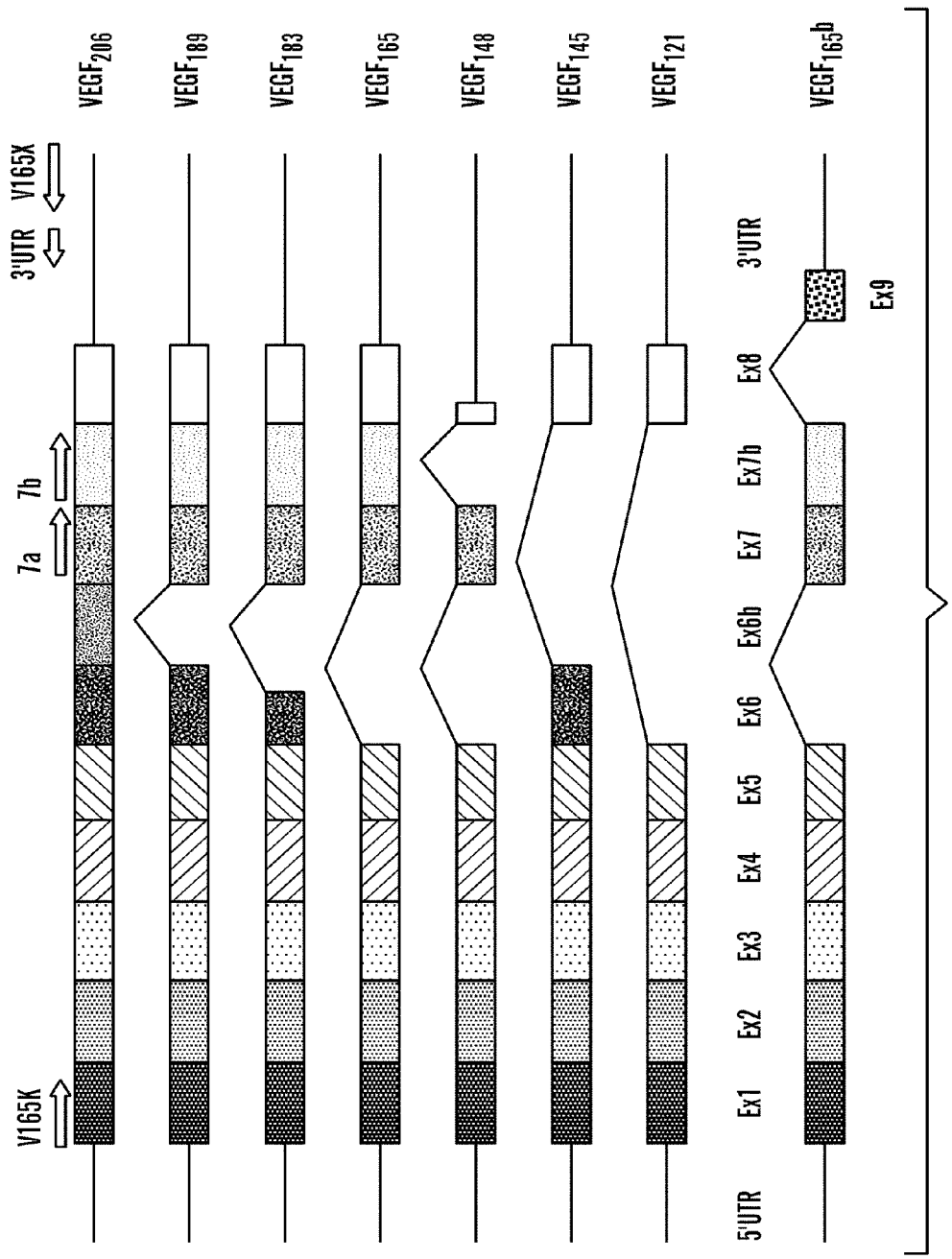

Immediately after nephrectomy, cubes of tissue were harvested from the periphery of a macroscopic human kidney tumour and from the benign cortical tissue of the opposite pole of the kidney. 100-200 mg of tissue was homogenised in Trizol reagent and mRNA extracted by addition of chloroform. The tissue was centrifuged and the aqueous layer removed into isopropanol. The mRNA was pelleted and resuspended in 20 μl DEPC treated water. 4 μl of RNA was reverse transcribed using MMLV RT and polydT as a primer. The cDNA was then amplified using 1 μM of the 3'UTR primer (ATGGATCCGTATCAGTCTTTCCT) (SEQ ID NO:3) and 1 μM of primers for either exon 7a (GTAAGCTTGTACAAGATCCGCAGACG) (SEQ ID NO:4), or exon 7b (GGCAGCTTGAGTTAAACGAACG) (SEQ ID NO:5), 1.2 mM M$_g$Cl$_2$, 2 mM dNTPs, and 1 unit of Taq polymerase (Abgene) in its buffer. Reactions were cycled 35 times, denaturing at 96° C. for 30 seconds, annealing at 55° C. for 30 seconds, and extending at 72° C. for 60 seconds. The position of annealing of the primers used to the VEGF isoforms is shown in FIG. 1.

Figure 2A:
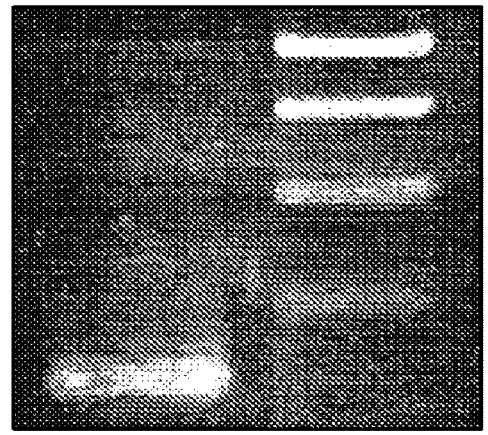
Figure 2B:
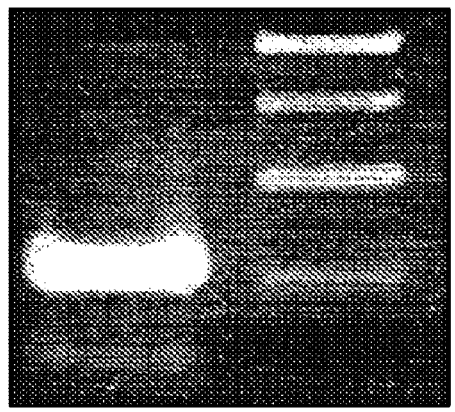

PCR products were run on a 3% agarose gel containing 0.5 μg/ml ethidium bromide and visualised under a UV transilluminator. Exon 7a and 3' UTR primers give a product consistent with VEGF$_{148}$ of 164 bp, and one consistent with VEGF$_{165, 183, 189}$ and $_{206}$ of 199 bp(see FIG. 2A). Exon 7b and 3' UTR primers give a product consistent with VEGF$_{165, 183, 189,}$ and $_{206}$ of 130 bp, but no product corresponding to VEGF$_{148}$ (see FIG. 2B). The band at 164 bp was excised from the gel under UV transillumination and the DNA extracted using Qiaex (Qiagen). The DNA was then digested with BamH1 and HinDIII and ligated into pBluescriptKSII (Stratagene). Ligations were transformed into supercompetent XL-1 Blue *E. coli* (Stratagene), and grown on ampicillin resistant LB agar plates. Colonies were amplified and the plasmid DNA purified using Qiagen columns. The DNA was then sequenced using T7 and T3 sequencing primers by fluorescent dideoxy termination sequencing (ABI370). Sequences were analysed by automated fluorescent chromatography, and the sequence checked against the chromatograph by eye.

The resulting sequence is shown in SEQ.ID No. 4.

In four of the samples the normal tissue had significantly more ~150 bp product than ~200 bp product. One of these samples was used to confirm the full length of the new isoform. The entire length of the product was amplified by RT-PCR using primers downstream of the original 3'UTR primer (V165X, AAT CTA GAC CTC TTC CTT CAT TTC AGG) (SEQ ID NO:6) engineered with an XbaI site, and a primer complementary to the translation intitiation site of the other isoforms of VEGF (V165K, CCG GTA CCC CAT GAA CTT TCT GC) (SEQ ID NO:7) engineered with a Kpn1 site and PCR conditions as previously described.

PCR was carried out using exon 7b and 3' UTR primers or exon 7a and 3' UTR primers and a selection of mRNAs purified from the opposite poles of four human kidneys as template RNA. By using opposite poles of the kidneys, both malignant tissue (at one pole) and benign tissue (at the other pole) samples were obtained from each of the four human kidneys studied. The PCR used the same reaction conditions as previously described.

Figure 3A:
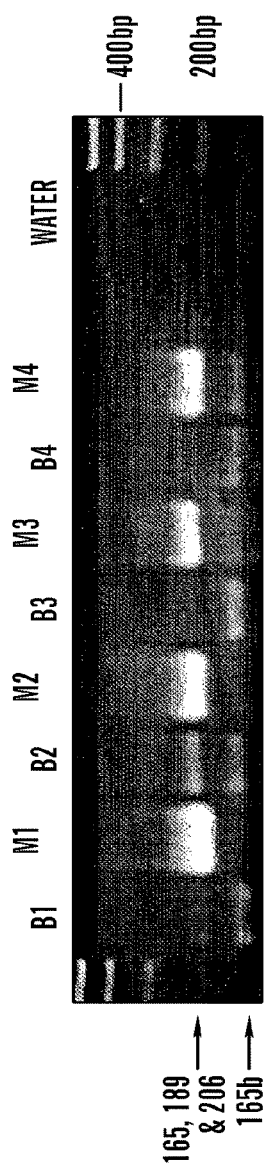
FIG. 3B is a box plot of the number of tissue samples with a band corresponding to VEGF165b (black) or without VEGF165b (stippled) in benign and malignant tissues.
Figure 3B:
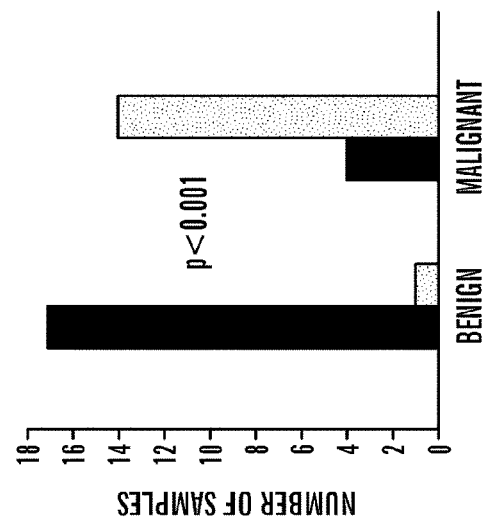

A sample of the results can be seen in FIG. 3. Of eighteen kidneys, 17 had detectable levels of expression of a VEGF isoform consistent with $VEGF_{148}$ in the benign tissue, whereas only 4 of the 18 kidney samples ($p<0.001$, Fishers Exact Test) had detectable levels of expression in the malignant tissue. Subsequent sequencing of this VEGF isoform revealed an unexpected 3' sequence (FIG. 4). The sequence indicated that the mRNA was spliced from the 3' end of exon 7 into the 3' untranslated region of $VEGF_{165}$ mRNA +44 by from the end of exon 8. This splice site has the same first two nucleotides as exon 8, but a different 3' sequence(see FIG. 4A), which has been designated exon9. The intronic region between exon 7 and exon 9 has an intronic consensus sequence of 5'GT . . . CAG3' and a high CT rich region 6-24 bp prior to the 5' end of exon 9. PCR of the full length product using primers V165K and V165X resulted in one strong band at approximately 670 bp. Further, nested PCR using the 3'UTR and 7a primers described above resulted in a strong band at 133 bp, confirming that the full length was $VEGF_{165}b$. Cloning of the full length of this sequence and subsequent sequence analysis using one of the clones (clone 1) revealed a 663 nucleotide sequence with a single open reading frame encoding a peptide 191 amino acids long. This peptide consisted of the same N terminal 185 amino acids as $VEGF_{165}$ (i.e.a 26 amino acid signal sequence followed by 159 amino acids corresponding to exons 1, 2, 3, 4, 5 and 7). However, the C terminal 6 amino acids were not the same as exon 8 (see FIG. 4B). The six amino acids that this new exon codes for are Ser-Leu-Thr-Arg-Lys-Asp (SEQ ID NO:9), followed by a stop codon, TGA. Since this splice variant would code for a mature 165 amino acid polypeptide (after cleavage of the signal sequence) with 96.4% identity with $VEGF_{165}$, this isoform has been designated $VEGF_{165}b$.

The region between exon 7 and exon 9 that has been spliced out in $VEGF_{165}b$ includes 66 by making up exon 8 and the first 44 by of the 3'UTR of $VEGF_{165}$. Therefore, the PCR product resulting from $VEGF_{165}b$ and exon 7+3'UTR primers is 66 by shorter than $VEGF_{165}$, hence the lower band seen on the gel in FIG. 3a which corresponds to the new VEGF isoform.

$VEGF_{148}$ lacks 35 nucleotides of exon 7, but retains the exon 8 nucleotide sequence (which remains untranslated due to the introduction of a stop codon due to a frame shift) and the untranslated region between exons 8 and 9, and the UTR 3' to exon 9. Therefore, the PCR product of $VEGF_{148}$ and exon 7+3'UTR primers would only be 31 by shorter than the $VEGF_{165}b$ PCR product using the same primers, hence the original observation that the lower band on the gel is consistent with $VEGF_{148}$. However, the lower band, in fact, corresponds to new isoform $VEGF_{165}b$.

Exons 8 and 9 both code for 6 amino acids and a stop codon. The amino acid sequences are completely different. Exon 8 encodes for CDKPRR (SEQ ID NO:24). The cysteine forms a disulphide bond with Cys146 in exon 7. This results in the carboxy terminus of $VEGF_{165}$ being held close to the receptor binding domain in exon 3 in the three dimensional structure of VEGF. In addition the proline inserts a kink in the amino acid backbone of the molecule to further appose the final three amino acids at the receptor binding domain. Finally the two terminal amino acids are highly positively charged arginine residues. These charged residues will be held very close to the receptor binding and in the crystal structure of the receptor ligand complex appear to be in a position to interact with the receptor. This, indicates that these amino acids may be necessary for receptor stimulation. Exon 9 on the other hand codes for SLTRKD (SEQ ID NO: 9) and has lost the cysteine residue and therefore the carboxy terminus may not be held into the receptor binding site. In addition there is no proline kink, and therefore the terminal two amino acids may not be able to interact with the receptor. It may therefore be possible that $VEGF_{165}b$ will bind to the VEGF receptor but not activate it. This theory arises since $VEGF_{165}b$ contains all the elements required for i) efficient dimerisation B $Cys^2$ and $Cys^4$ in exon 3 (21); ii) receptor binding B for VEGFR1 Asp63, Glu64, Glu67 in exon 3, for VEGFR2 Arg82, Lys84, His 86 in exon 4, and for neuropilin-1 Cys136 to Cys158 in exon 7. This isoform substitutes exon 9 for exon 8 and therefore has no Cys159 which normally binds to Cys146 in exon 7, and will therefore be likely to affect the folding and tertiary structure of the VEGF molecule.

The fact that this isoform has been found specifically in the kidney is particularly interesting as the kidney, and in particular the glomerulus has been shown to produce high levels of VEGF. This has always been assumed to be $VEGF_{165}$, since it is detected by antibodies to $VEGF_{165}$, in situ hybridisation using probes to $VEGF_{165}$, PCR using primers specific to $VEGF_{165}$ and so on. However, in almost all these cases the detection techniques used would not distinguish between $VEGF_{165}$ and $VEGF_{165}b$. The only reason that $VEGF_{165}b$ has been detected now is that an attempt was being made to examine $VEGF_{148}$ expression in this tissue. It is interesting that, despite high levels of VEGF produced by podocytes in the glomerulus, glomerular endothelial cells, which do express VEGF receptors, are not of an angiogenic phenotype. Endothelial cell turnover in the glomerulus is low, as in other parts of the body, and there is no overt angiogenesis occurring. This apparent paradox—high VEGF expression but low angiogenesis—may be explained by $VEGF_{165}b$. Kidney tumours must grow in an environment in which VEGF is highly expressed under normal conditions, and yet angiogenesis is prevented. Therefore tumours need to overcome some endogenous anti-angiogenic process in order to grow. If $VEGF_{165}b$ is inhibitory then the down regulation of $VEGF_{165}b$ by tumours, as shown here, would be necessary for tumours to switch angiogenesis on in this tissue. Furthermore, the high production of VEGF by the glomerulus may actually be $VEGF_{165}b$ rather than $VEGF_{165}$, and therefore this would explain why angiogenesis is not observed.

A further clone (clone 2) containing the full length PCR product (obtained using primers V165K and V165X) was selected and sequenced. Surprisingly, although this sequence contained the same C terminal 6 amino acids as clone 1, indicating the presence of exon 9, the full length of the cloned sequence was longer than that of the sequence of clone 1, i.e. longer than 670 by and therefore not consistent with $VEGF_{165}b$. In fact, the sequence length was found to be slightly over 700 bp, which is more consistent with $VEGF_{183}b$ (see FIG. 5). FIG. 5B shows the products of nested PCR using the excised ~700 by band as template and exon 7 and 3'UTR as primer pairs.

It therefore seems that a family of VEGF isoforms may exist which posses exon 9 in place of exon 8. The existence of $VEGF_{165}b$ has been demonstrated in the example provided hereinand and evidence for $VEGF_{183b}$ is presented. However, it is likely that similar isoforms exist which correspond to $VEGF_{121}$, $VEF_{145}$, $VEGF_{189}$, $VEGF_{206}$, designated $VEGF_{121}b$, $VEGF_{145}b$, $VEGF_{189}b$ and $VEGF_{206}b$. These isoforms which lack exon 8 are all expected to demonstrate anti-angiogenic activity.

TABLE 1

Expected PCR product size for V165K and V165X primers for the different splice variants of VEGF.

| No of amino acids | 121 | 145 | 148 | 165 | 183 | 189 | 206 |
|---|---|---|---|---|---|---|---|
| No of $VEGF_{xxx}$ | 597 | 669 | 694 | 729 | 783 | 801 | 852 |
| nucleotide $VEGF_{xxx}b$ s3' | 531 | 603 | 628 | 663 | 717 | 735 | 786 |

EXAMPLE 2

In separate transfections, full length $VEGF_{165}b$ cDNA and full length $VEGF_{165}$ cDNA were cloned into pcDNA3 using standard methodology, and then transfected into HEK 293 cells and a stable cell line generated using Geneticin selection. Confluent cells were incubated in basal M200 endothelial cell medium for 48 hours containing neither serum nor Geneticin, and the conditioned media assayed for VEGF concentration using a pan VEGF ELISA (R & D Systems). Control (mock) conditioned media (pcDNA3-CM) was collected in the same way from HEK293 cells transfected with pcDNA3 only.

Freshly isolated HUVECs incubated in 0.1% serum M200 overnight were incubated with either pcDNA3-CM, $VEGF_{165}$-CM (adjusted to 100 ng/ml $VEGF_{165}$ with pcDNA3-CM), $VEGF_{165}b$-CM (adjusted to 100 ng/ml $VEGF_{165}b$ with pcDNA3-CM) or a mixture of $VEGF_{165}b$-CM and $VEGF_{165}$-CM (adjusted to 100 ng/ml $VEGF_{165}b$ and 100 ng/ml $VEGF_{165}$ with pcDNA3-CM), and then 37 kBq of $^3$H-Thymidine (Amersham Pharmacia) added. After 4 hrs the cells were washed, trypsinised, cell number counted on a hemocytometer and radioactivity measured on a beta counter (LKB-1217). Incorporation was calculated as counts per cell. Dose response curves were carried out in a similar manner, except that $VEGF_{165}b$-CM was diluted with pcDNA3-CM and 50 ng/ml $VEGF_{165}$ (Peprotech, N.J.) added. Proliferation index was calculated as $^3$H-thymidine incorporation of $VEGF_{165}$ treated cells compared to mean incorporation into cells with no $VEGF_{165}$ treatment.

To determine the functional effect of $VEGF_{165}b$ we measured endothelial cell proliferation by determination of $^3$H-thymidine incorporation per cell number during incubation with conditioned media from transfected cells (FIG. 6). The full-length cDNA generated by PCR was cloned into an expression vector (pcDNA3-$VEGF_{165}b$), as was full length $VEGF_{165}$ (pcDNA3-$VEGF_{165}$) and each transfected into HEK293 cells. The VEGF concentration of cell conditioned media ($VEGF_{165}b$-CM), as determined by ELISA using pan VEGF antibodies, ranged from 80-400 ng/ml VEGF. Conditioned media from cells transfected with pcDNA3-$VEGF_{165}$ ($VEGF_{165}$-CM) had a VEGF concentration of 100-260 ng/ml. Media from cells transfected with pcDNA3 alone (pcDNA3-CM) contained <62.5 pg/ml VEGF (the minimum detection limit of the ELISA). HUVECs were incubated in $VEGF_{165}$-CM adjusted to 100 ng/ml (with pcDNA3-CM) and this resulted in a significant 283±43% increase in thymidine incorporation per endothelial cell compared to pcDNA3-CM alone (P<0.01, ANOVA, FIG. 6a). $VEGF_{165}b$-CM containing 100 ng/ml $VEGF_{165}b$ did not stimulate HUVEC proliferation (165±27% of pcDNA3-CM, no significant increase, but significantly less than $VEGF_{165}$-CM, p<0.05). Furthermore, there was no increase in endothelial cell proliferation when cells were incubated in a combination of both $VEGF_{165}b$-CM and $VEGF_{165}$-CM containing 100 ng/ml of each VEGF isoform (150±18% of pcDNA3-CM, not significantly different from pcDNA3-CM, but significantly lower than $VEGF_{165}$-CM, p<0.05). Therefore $VEGF_{165}b$ did not stimulate HUVEC proliferation, and moreover, significantly inhibited $VEGF_{165}$ stimulated proliferation. Furthermore when endothelial cells were incubated in CM containing increasing concentrations of $VEGF_{165}b$ there was a dose dependent inhibition of $^3$H-thymidine incorporation stimulated by commercially available $VEGF_{165}$ (FIG. 6b), with a molar ratio $IC_{50}$ of 0.94 (FIG. 6d) (i.e. equimolar inhibition). Additionally, $VEGF_{165}b$-CM did not affect FGF mediated proliferation (FIG. 6c).

EXAMPLE 3

The effect of $VEGF_{165}b$ on $VEGF_{165}$-mediated vasodilatation was determined as detailed below.

$3^{rd}$ order superior mesenteric arteries were dissected from 200-300 g male Wistar rats (sacrificed by stunning and cervical dislocation) and leak-free segments mounted in an arteriograph at 80 mmHg, in M200 media 10 mm acetylcholine (Ach) maximally dilated all arteries used in this example, demonstrating the presence of an intact endothelium.

The rat mesenteric arteries were preconstricted with 0.6-1 µm phenylephrine (PE) applied in the superfusate (see FIG. 7A). Ach, CM and VEGF isoforms (all dialysed against rat ringer solution using 3500 MW dialysis tubing) were then applied to the lumen of the artery using an adaptation of the Halpern pressure myograph technique as described in Doughty, J. M. et al (1999) *Am J Phusiol* 276, 1107-12. The concentration of VEGF in the CM after dialysis was determined by ELISA. All data are expressed as mean values±s.e. mean for 4 experiments. Statistical significance was tested using ANOVA and Student Newmann Keuls post-hoc test.

We measured the effects of $VEGF_{165}b$ on vasodilatation to determine whether $VEGF_{165}b$ could inhibit the effects of $VEGF_{165}$ on intact vessels. Luminal perfusion of isolated pressurized rat mesenteric arteries in vitro with pc-DNA3-CM resulted in no change in vessel diameter (FIG. 7). Perfusion of the same arteries with dialyzed $VEGF_{165}b$-CM (40 ng/ml) did not affect the diameter of the arteries either. Perfusion with dialyzed CM containing 20 ng/ml $VEGF_{165}$ resulted in significant vasodilatation, but this vasodilatation was abolished when perfused with $VEGF_{165}b$-CM and $VEGF_{165}$ (40 ng/ml $VEGF_{165}b$, 20 ng/ml $VEGF_{165}$). Therefore $VEGF_{165}b$ does not stimulate vasodilatation, and is also capable of inhibiting $VEGF_{165}$-mediated vasodilatation.

EXAMPLE 4

As mentioned earlier, the kidney, and in particular the glomerulus, has been shown to produce high levels of VEGF. This has always been assumed to be $VEGF_{165}$, since it is detected by antibodies to $VEGF_{165}$, or by in situ hybridisation using probes to $VEGF_{165}$, or by PCR using primers specific to $VEGF_{165}$.

However, in all of these cases, the detection techniques used would not distinguish between $VEGF_{165}$ and $VEGF_{165}b$.

A method of detection of $VEGF_{165}b$ mRNA independently of $VEGF_{165}$ mRNA has been developed and is detailed below (FIGS. 8 and 9A).

PCR was carried out using vectors containing $VEGF_{165}$ and $VEGF_{165}b$, respectively, and the following primers:

```
Forward primer
Exon-4
GAGATGAGCTTCCTACAGCAC            (SEQ ID NO: 1)

Reverse Primer
9H
TTAAGCTTTCAGTCTTTCCTGGTGAGAGATCTGCA  (SEQ ID NO: 2)
```

The annealing and denaturing steps were carried out for 30 seconds and denaturing was carried out at 94° C. 1 minute periods of extension were carried out at 72° C.

As can be seen from FIG. 8, when an annealing temperature of 58° C. is used, PCR products are obtained for both $VEGF_{165}$ and $VEGF_{165}b$. However, when an annealing temperature of 60° C. is used, there is no cross-reactivity and no PCR product corresponding to $VEGF_{165}$ is obtained.

Competitive PCR studies were carried out using the PCR primers and conditions mentioned above, with the annealing step being carried out at 60° C. The samples used contained $VEGF_{165}$ and $VEGF_{165}b$ at various relative concentrations, as shown in FIG. 9a. FIG. 9a demonstrates that, even when $VEGF_{165}$ is present in the sample at 1000 times the concentration at which $VEGF_{165}b$ is present, the only PCR product obtained corresponds to amplification of $VEGF_{165}b$ and not $VEGF_{165}$.

Therefore, the above primers can be used to detect $VEGF_{165}$ and $VEGF_{165}b$ in a sample. Further, by altering the temperature at which the PCR annealing step is carried out, the same primers can be used to specifically detect the presence of $VEGF_{165}b$ in a sample containing both $VEGF_{165}$ and $VEGF_{165}b$.

EXAMPLE 5

Full length $VEGF_{165}b$ or $VEGF_{165}$ (generated by PCR from tissue) was cloned into the expression vector $pcDNA_3$ using standard methodology, and then transfected into HEK 293 cells and a stable cell line generated using Geneticin selection. Confluent cells were incubated in basal M200 endothelial cell medium for 48 hours, containing neither serum nor Geneticin, and the conditioned media assayed for VEGF concentration using a pan VEGF ELISA(R&D). Control conditioned media (pcDNA3-CM) was collected in the same way from HEK293 cells stably transfected with $pcDNA_3$. FIG. 9b shows a Western blot of conditioned media from $VEGF_{165}b$ transfected cells ($VEGF_{165}b$-CM) and $VEGF_{165}$ transfected cells ($VEGF_{165}$-CM). $VEGF_{165}b$ was the same molecular weight as $VEGF_{165}$, and both isoforms correspond to previously published molecular weights for $VEGF_{165}$ (Ferrara N et al Biophys. Res. Comm. 1989; 161: 851-8). The blot also confirms that most of the $VEGF_{165}$ and $VEGF_{165}b$ made in HEK cells had a slightly greater molecular weight than commercially available $VEGF_{165}$ (23 kDa compared to 18 kDa). This is probably due to the fact that commercially available $VEGF_{165}$ is not glycosylated. There was some $VEGF_{165}b$ and $VEGF_{165}$ in the conditioned media that appeared to be de-glycosylated, but this was a small fraction of the total VEGF.

EXAMPLE 6 mRNA from sixteen different tissues was reverse transcribed and amplified using exon 7 and 3'UTR primers. PCR products of lengths consistent with expression of exon 9 containing isoforms were clearly detected in umbilical cord, cerebrum, aorta, prostate, pituitary, lung, skeletal muscle and placental tissue as well as kidney (see FIG. 10A). Fainter bands were also seen in colon, skin, bladder and spinal cord. No significant exon 9-containing isoforms were detected in the hypothalamus, inferior vena cava (IVC), or liver. Subsequent PCR using exon 9-specific primers confirmed the distribution of expression in the different tissues (see FIG. 10B), but in this case expression was detected in liver, and expression in the pituitary was marginal. Interestingly in aorta, prostate and umbilical cord a slightly longer band was seen. It is not clear whether these are additional exon 9-containing isoforms such as $VEGF_{183}b$ and/or $VEGF_{189}b$.

EXAMPLE 7

In order to assess the functional properties of $VEGF_{165}b$ on endothelial cell migration, migration assays were performed in a modified 24-well Boyden chamber containing collagen coated polycarbonate filter inserts (8 µm pore; Millipore). The filters were placed in 24 well plates containing 0.5 ml per well of either 1) $VEGF_{165}$-CM containing 33 ng/ml $VEGF_{165}$; 2) $VEGF_{165}b$-CM containing 33 ng/ml $VEGF_{165}b$; 3) $VEGF_{165}$-CM and $VEGF_{165}b$-CM (33 ng/ml of each isoform); or 4) $pcDNA_3$-CM. HUVECs were suspended in serum free medium and 25,000 cells added to the upper chamber of each well. The plate was incubated for 6 h to allow migration, media removed and both chambers washed with PBS (×2). 0.2 mg/ml Thiazolyl Blue (MTT) in media was then added to both chambers and incubated for 3 h at 37° C. The media was removed and the chambers were washed with PBS (×2). Non-migrated cell crystals in the upper chamber (stained blue) were removed with a cotton swab, which was placed in 1 ml of Dimethyl Sulphoxide (DMSO) to dissolve the MTT product. Migratory cell crystals (on the underside of the insert) were also dissolved in MTT. The samples were left overnight to permit complete solution of the product. The absorbance of soluble MTT was determined at a wavelength of 570 nm using a spectrophotometer. The percentage migration was then calculated from the intensity of the lower well as a percentage of the total intensity of both wells. Assays were run in sextuplet.

HUVECs were incubated in $VEGF_{165}$-CM (33 ng/ml $VEGF_{165}$) and this resulted in a significant 24±3% increase in migration of endothelial cells compared to pcDNA3-CM alone (P<0.01, ANOVA) (FIG. 11). $VEGF_{165}b$ -CM containing 33 ng/ml $VEGF_{165}b$ did not stimulate migration (−3±2.6% compared to pcDNA3-CM, not significant). Furthermore, there was no increase in migration when cells were incubated in a combination of both $VEGF_{165}b$-CM and $VEGF_{165}$-CM containing 33 ng/ml of each isoform (9.9±5.8% compared to pcDNA3-CM). Therefore $VEGF_{165}b$ did not stimulate migration, and again significantly inhibited $VEGF_{165}$-stimulated migration (P<0.001, ANOVA).

EXAMPLE 8

A search of the nucleotide database provides interesting information on the conservation of the 3' untranslated region (3'UTR). The entire 3' UTR from the end of exon 8 is 100% conserved between human and macaque. In other mammalian species there is relatively good conservation of the supposed 3' UTR terminal to exon 8 (FIG. 12). In fact, in the cow the mRNA has >95% identity in the 66 bases 3' to the stop codon of exon 8, and exon 9 is >90% identical. However, this identity breaks down immediately after the exon 9 stop codon (see FIG. 12). There is significantly less identity in the 22 bases after this stop codon (53%) than that in exon 9 (91%). This pattern is also evident in mouse where the exon 9 containing sequence is 86% identical to human, but only 23% identical in the 22 base pairs immediately after the exon 9 stop codon (see FIG. 12). Interestingly the mouse sequence predicts an exon 9 of 7 amino acids of the sequence PLTGKTD (SEQ ID NO:8), compared to SLTRKD (SEQ ID NO:9) in the human and macaque and RLTRKD (SEQ ID NO:10) in the cow. Therefore 4 out of six amino acids are conserved [XLTXK(X)D] (SEQ ID NO:25) and this appears to have been brought about by a double mutation—an adenosine insertion in the human at nucleotide 10 (mouse) and a cytosine to thymidine mutation at nucleotide 19 (mouse) that rescues the stop codon (see FIG. 12). This is indirect evidence for functional relevance of the splice site. Interestingly it is only conserved in mammals, not in birds or fish.

EXAMPLE 9

VEGF has been shown to be massively upregulated in arthritis, particularly in synovial fibroblasts, macrophages and synovial lining cells (Nagashima M et al, 1995; J Rheumatol 22: 1624-30). Furthermore there is now mounting functional evidence that inhibition of angiogenesis, both non-specifically with pharmacological anti-angiogenic agents (Oliver S et al Cell Immunol 1994; 157: 291-9; Oliver S. et al Cell Immunol 1995; 166: 196-206), and specifically with anti-VEGF agents, ameliorates the joint lesions in well characterised animal models of arthritis (Miolta J et al Lab Invest 2000; 80: 1195-205; Sone H et al Biochem Biophys Res Commun 2001; 281: 562-8). Using an RT-PCR protocol described under example 6, $VEGF_{165}b$ expression has been identified in human synovium (taken at operation from a patient who suffered a fractured neck of femur secondary to osteoporosis). $VEGF_{165}b$ expression was shown to be present in normal human synovium collected from the Bristol University Anatomy Department. In order to obtain preliminary data on the expression of $VEGF_{165}b$ mRNA in normal and arthritic tissue, RT-PCR was carried out on two previously available samples of osteo tissue and two of rheumatoid tissue (see FIG. 13). Interestingly $VEGF_{165}b$ was found in three of these four samples, but at a lower level than $VEGF_{165}$. This was in stark contrast to normal tissue which had at least as much $VEGF_{165}b$ as $VEGF_{165}$. The ratio of $VEGF_{165}b$ to $VEGF_{165}$ mRNA in synovium was therefore, lower in rheumatoid arthritis than osteoarthritis, and lower in osteoarthritis than normal tissue. This suggests that in arthritis the anti-angiogenic properties of $VEGF_{165}b$ also are reduced.

EXAMPLE 10

Human islet transplantation offers a unique therapeutic option in the management of the metabolic and vascular sequelae of diabetes mellitus. However animal models and clinical experience suggest that transplanted islet function is not predictable in an individual recipient. It has been suggested that the initial function of transplanted islets is dependent on their ability to access the recipient vascular system by the stimulation of microvascular angiogenesis.

Human islets were purified by collagenase digestion (Liberase HI, Roche Diagnostics) and continuous density gradient centrifugation on a Cobe 2991 cell separator. Individual islets were then collected in 20 µl diethylpyrocarbonate (depc) $H_2O$ in separate tubes. Each sample was homogenized in Trizol reagent and mRNA was extracted according to the manufacturers' instructions. mRNA was reverse transcribed using polyd(T) as a primer and ExpandRT (Roche). Exon 8 and exon 9 containing VEGF isoforms were studied in 11 individual islets. A heterogeneity of expression of both VEGF families was identified (see FIG. 14). It is believed that the balance of pro- and anti-angiogenic VEGF isoform expression by transplanted islets may determine the survival of individual islets and hence the overall efficiency of the graft. Inhibition of the activity of anti-angiogenic $VEGF_{165}b$ may therefore enhance graft survival and function.

EXAMPLE 11

In order to assess if $VEGF_{165}b$ expression is altered in cancers other than renal cancer, $VEGF_{165}b$ expression was studied in prostate.

VEGF165b expression was studied in trans-urethral prostatectomy curettings using the PCR protocol described under example 6 (Exon specific primers). VEGF165b was present in significantly less malignant samples compared to benign (FIG. 15).

In addition, we studied VEGF165b expression in archival radical prostatectomy samples to determine the expression of VEGF165b in the early stages of prostate cancer, i.e. in prostatic intra-epithelial neoplasia (PIN)(see FIG. 16). Significant down regulation of VEGF165b mRNA was seen in PIN lending credence to the hypothesis that the angiogenic switch in prostate cancer may result from an imbalance of pro and anti-angiogenic VEGF isoforms. The template mRNA was obtained from archival tissue using a standard protocol (Krafft A E I et al. (1997); 2(3); 217-230).

EXAMPLE 12

To assess the possibility of specifically inhibiting the $VEGF_{165}b$ isoform, small interference RNAs to the exon 7-exon 9 boundary were developed.

siRNA probes may be made according to the art from primers for example of the sequence:

```
T7siRNA165bsR
                                       (SEQ ID NO: 11)
5' AGAGATCTGCAAGTACGTTCTATAGTGAGTCGTATTA 3'

T7siRNA165basR
                                       (SEQ ID NO: 12)
5' ACGAACGTACTTGCAGATCTCTATAGTGAGTCGTATTA 3' siRNA165bF
                                       (SEQ ID NO: 13)
5' TAATACGACTCACTATAG 3'
```

These are T7 small interfering RNA for $VEGF_{165}b$ sense reverse primer, T7 small interfering RNA for $VEGF_{165}b$ antisense reverse primer and small interference RNA for $VEGF_{165}b$ forward primer, respectively.

Production of double stranded DNA duplexes from T7siRNA165bsR and T7siRNA165bF provide templates for sense RNA, and production of double stranded DNA duplexes from T7siRNA165basR and siRNA165bF provide templates for antisense RNA.

Annealing of these two RNAs results in the production of a double stranded siRNA duplex with overhang of the sequence (SEO ID NOS:14 & 26, respectively in order of appearance):

```
5'   GAACGUACUUGCAGAUCUCUC 3'
     |||||||||||||||||||||
3' UGCUUGCAUGAACGUCUAGAG    5'
```

This double stranded siRNA duplex, when transfected into cells, will reduce VEGF$_{165}$b production, as shown in FIG. 17.

(SEQ ID NO: 9)-Amino acid sequence of Exon 9
SLTRKD

SEQ ID NO: 16)-Nucleotide sequence of Exon 9
ATCTCTCACCAGGAAAGACTGA (SEQ ID NO: 17)-Amino acid sequence of VEGF$_{165}$b
MNFLLSWVHW SLALLLYLHH AKWSQAAPMA EGGGQNHHEV
VKFMDVYQRSYCHPIETLVD IFQEYPDEIE YIFKPSCVPL
MRCGGCCNDE GLECVPTEESNITMQIMRIK PHQGQHIGEM
SFLQHNKCEC RPKKDRARQE NPCGPCSERRKHLFVQDPQT
CKCSCKNTDS RCKARQLELN ERTCR SLTRK D (SEQ ID NO: 18)-Nucleotide sequence of VEGF$_{165}$b
ATGA ACTTTCTGCT GTCTTGGGTG CATTGGAGCC TTGCCTTGCT
GCTCTACCTC CACCATGCCA AGTGGTCCCA GGCTGCACCC
ATGGCAGAAG GAGGAGGGCA GAATCATCAC GAAGTGGTGA
AGTTCATGGA TGTCTATCAG CGCAGCTACT GCCATCCAAT
CGAGACCCTG GTGGACATCT TCCAGGAGTA CCCTGATGAG
ATCGAGTACA TCTTCAAGCC ATCCTGTGTG CCCCTGATGC
GATGCGGGGG CTGCTGCAAT GACGAGGGCC TGGAGTGTGT
GCCCACTGAG GAGTCCAACA TCACCATGCA GATTATGCGG
ATCAAACCTC ACCAAGGCCA GCACATAGGA GAGATGAGCT
TCCTACAGCA CAACAAATGT GAATGCAGAC CAAAGAAAGA
TAGAGCAAGA CAAGAAAATC CCTGTGGGCC TTGCTCAGAG
CGGAGAAAGC ATTTGTTTGT ACAAGATCCG CAGACGTGTA
AATGTTCCTG CAAAAACACA GACTCGCGTT GCAAGGCGAG
GCAGCTTGAG TTAAACGAAC GTACTTGCAG ATCT CTCACCAGGA
AAGACTGA

---

The invention claimed is:

1. An isolated antibody against a polypeptide which (i) inhibits pro-angiogenic VEGF receptors activity and (ii) comprises an amino acid sequence at least 80% identical to the C-terminal 165 amino acid sequence from SEQ ID NO:17, wherein the antibody comprises exon 9 specific binding functionality, wherein "exon 9" refers to the C-terminal sequence of SEQ ID NO:17 consisting of amino acids SLTRKD set forth in SEQ ID NO:9.

* * * * *

SEQUENCE LISTING

<160> NUMBER OF SEQ ID NOS: 31

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagatgagct tcctacagca c                                            21

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttaagctttc agtctttcct ggtgagagat ctgca                             35

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atggatccgt atcagtcttt cct                                          23

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtaagcttgt acaagatccg cagacg                                       26

<210> SEQ ID NO 5
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 5
ggcagcttga gttaaacgaa cg                                              22

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aatctagacc tcttccttca tttcagg                                         27

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccggtacccc atgaactttc tgc                                             23

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Leu Thr Gly Lys Thr Asp
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Leu Thr Arg Lys Asp
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Leu Thr Arg Lys Asp
1               5

<210> SEQ ID NO 11
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agagatctgc aagtacgttc tatagtgagt cgtatta                              37

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acgaacgtac ttgcagatct ctatagtgag tcgtatta                             38

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taatacgact cactatag                                                   18

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaacguacuu gcagaucucu c                                               21

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Leu Thr Arg Lys Asp
1               5

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atctctcacc aggaaagact ga                                              22

<210> SEQ ID NO 17
<211> LENGTH: 191
<212> TYPE: PRT
```

<213> ORGANISM: Homo sapiens

<400> SEQUENCE: 17

```
Met Asn Phe Leu Leu Ser Trp Val His Trp Ser Leu Ala Leu Leu Leu
1               5                   10                  15
Tyr Leu His His Ala Lys Trp Ser Gln Ala Ala Pro Met Ala Glu Gly
            20                  25                  30
Gly Gly Gln Asn His His Glu Val Val Lys Phe Met Asp Val Tyr Gln
        35                  40                  45
Arg Ser Tyr Cys His Pro Ile Glu Thr Leu Val Asp Ile Phe Gln Glu
    50                  55                  60
Tyr Pro Asp Glu Ile Glu Tyr Ile Phe Lys Pro Ser Cys Val Pro Leu
65                  70                  75                  80
Met Arg Cys Gly Gly Cys Cys Asn Asp Glu Gly Leu Glu Cys Val Pro
                85                  90                  95
Thr Glu Glu Ser Asn Ile Thr Met Gln Ile Met Arg Ile Lys Pro His
            100                 105                 110
Gln Gly Gln His Ile Gly Glu Met Ser Phe Leu Gln His Asn Lys Cys
        115                 120                 125
Glu Cys Arg Pro Lys Lys Asp Arg Ala Arg Gln Glu Asn Pro Cys Gly
    130                 135                 140
Pro Cys Ser Glu Arg Arg Lys His Leu Phe Val Gln Asp Pro Gln Thr
145                 150                 155                 160
Cys Lys Cys Ser Cys Lys Asn Thr Asp Ser Arg Cys Lys Ala Arg Gln
                165                 170                 175
Leu Glu Leu Asn Glu Arg Thr Cys Arg Ser Leu Thr Arg Lys Asp
            180                 185                 190
```

<210> SEQ ID NO 18
<211> LENGTH: 576
<212> TYPE: DNA
<213> ORGANISM: Homo sapiens

<400> SEQUENCE: 18

```
atgaactttc tgctgtcttg ggtgcattgg agccttgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgcccctg     240
atgcgatgcg ggggctgctg caatgacgag ggcctggagt gtgtgcccac tgaggagtcc     300
aacatcacca tgcagattat gcggatcaaa cctcaccaag ccagcacat aggagagatg     360
agcttcctac agcacaacaa atgtgaatgc agaccaaaga agatagagc aagacaagaa     420
aatccctgtg ggccttgctc agagcggaga aagcatttgt ttgtacaaga tccgcagacg     480
tgtaaatgtt cctgcaaaaa cacagactcg cgttgcaagg cgaggcagct tgagttaaac     540
gaacgtactt gcagatctct caccaggaaa gactga                               576
```

<210> SEQ ID NO 19
<211> LENGTH: 152
<212> TYPE: DNA
<213> ORGANISM: Homo sapiens

<400> SEQUENCE: 19

```
aaggcgaggc agcttgagtt aaacgaacgt acttgcagat gtgacaagcc gaggcggtga      60
gccgggcagg aggaaggagc ctccctcagg gtttcgggaa ccagatctct caccaggaaa     120
```

-continued

```
gactgataca gaacgatcga tacagaaacc ac                                    152
```

<210> SEQ ID NO 20
<211> LENGTH: 24
<212> TYPE: PRT
<213> ORGANISM: Homo sapiens

<400> SEQUENCE: 20

Thr Asp Ser Arg Cys Lys Ala Arg Gln Leu Glu Leu Asn Glu Arg Thr
1               5                   10                  15

Cys Arg Cys Asp Lys Pro Arg Arg
            20

<210> SEQ ID NO 21
<211> LENGTH: 69
<212> TYPE: DNA
<213> ORGANISM: Bos sp.

<400> SEQUENCE: 21

```
acgtctcacc aggaaagact gacacagaac tacccatagc cgccgccacc accaccacac      60
caccaccac                                                             69
```

<210> SEQ ID NO 22
<211> LENGTH: 69
<212> TYPE: DNA
<213> ORGANISM: Homo sapiens

<400> SEQUENCE: 22

```
atctctcacc aggaaagact gatacagaac gatcgataca gaaaccacgc tgccgccacc      60
acaccatca                                                             69
```

<210> SEQ ID NO 23
<211> LENGTH: 68
<212> TYPE: DNA
<213> ORGANISM: Mus sp.

<400> SEQUENCE: 23

```
acctctcacc ggaaagaccg attaaccatg tcaccaccat gccatcatcg tcaccgttga      60
cagaacag                                                              68
```

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Asp Lys Pro Arg Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: variable amino acid
<220> FEATURE:
<221> NAME/KEY: MOD_RES

```
<222> LOCATION: (4)..(4)
<223> OTHER INFORMATION: variable amino acid
<220> FEATURE:
<221> NAME/KEY: MOD_RES
<222> LOCATION: (6)..(6)
<223> OTHER INFORMATION: variable amino acid

<400> SEQUENCE: 25

Xaa Leu Thr Xaa Lys Xaa Asp
1               5

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gagaucugca aguacguucg u                                              21

<210> SEQ ID NO 27
<211> LENGTH: 86
<212> TYPE: DNA
<213> ORGANISM: Homo sapiens

<400> SEQUENCE: 27
aaggcgaggc agcttgagtt aaacgaacgt acttgcagat ctctcaccag gaaagactga    60
tacagaacga tcgatacaga aaccac                                         86

<210> SEQ ID NO 28
<211> LENGTH: 70
<212> TYPE: DNA
<213> ORGANISM: Homo sapiens

<400> SEQUENCE: 28
acagactcgc gttgcaaggc gaggcagctt gagttaaacg aacgtacttg caggttggtt    60
cccagaggca                                                           70

<210> SEQ ID NO 29
<211> LENGTH: 63
<212> TYPE: DNA
<213> ORGANISM: Homo sapiens

<400> SEQUENCE: 29
ttttccattt ccctcagatg tgacaagccg aggcggtgag ccgggcagga ggaaggagcc    60
tcc                                                                  63

<210> SEQ ID NO 30
<211> LENGTH: 68
<212> TYPE: DNA
<213> ORGANISM: Homo sapiens

<400> SEQUENCE: 30
ctcagggttt cgggaaccag atctctcacc aggaaagact gatacagaac gatcgataca    60
gaaaccac                                                             68

<210> SEQ ID NO 31
<211> LENGTH: 24
<212> TYPE: PRT
<213> ORGANISM: Homo sapiens

<400> SEQUENCE: 31
```

```
Thr Asp Ser Arg Cys Lys Ala Arg Gln Leu Glu Leu Asn Glu Arg Thr
1               5                   10                  15

Cys Arg Ser Leu Thr Arg Lys Asp
                20
```